US008885174B2

(12) United States Patent
Jourdain et al.

(10) Patent No.: US 8,885,174 B2
(45) Date of Patent: Nov. 11, 2014

(54) MONITORING ENERGY AND MATTER FLUXES BY USE OF ELECTROMAGNETIC RADIATIONS

(75) Inventors: Pascal Jourdain, Sergy (FR); Etienne Cuche, Maracon (CH); Christian Depeursinge, Preverenges (CH); Pierre Julius Magistretti, Epalinges (CH); Pierre Marquet, Cheseaux-sur-Lausanne (CH)

(73) Assignee: Lyncee Tec S.A., Lausanne (CH)

( * ) Notice: Subject to any disclaimer, the term of this patent is extended or adjusted under 35 U.S.C. 154(b) by 494 days.

(21) Appl. No.: 13/203,189

(22) PCT Filed: Feb. 19, 2010

(86) PCT No.: PCT/IB2010/050747
§ 371 (c)(1),
(2), (4) Date: Oct. 21, 2011

(87) PCT Pub. No.: WO2010/097743
PCT Pub. Date: Sep. 2, 2010

(65) Prior Publication Data
US 2012/0038931 A1 Feb. 16, 2012

(30) Foreign Application Priority Data
Feb. 24, 2009 (WO) .................. PCT/IB2009/050733

(51) Int. Cl.
*G01N 21/45* (2006.01)
*G03H 1/04* (2006.01)
*G03H 1/00* (2006.01)

(52) U.S. Cl.
CPC ............. *G01N 21/45* (2013.01); *G03H 1/0443* (2013.01); *G03H 2210/63* (2013.01); *G03H 2001/0033* (2013.01)
USPC ......................................................... 356/518

(58) Field of Classification Search
CPC ............... G01B 9/021; G01B 9/02047; G01B 9/02098; G01B 11/164
USPC .................................................. 356/517, 518
See application file for complete search history.

(56) References Cited

U.S. PATENT DOCUMENTS

2005/0036181 A1 2/2005 Marquet et al.
2008/0265130 A1 10/2008 Colomb et al.

FOREIGN PATENT DOCUMENTS

DE 29 10 428 9/1980
DE 195 11 473 10/1995

OTHER PUBLICATIONS

International Preliminary Report on Patentability (IPRP) (Chapter I) for PCT/IB2010/050747, issued Feb. 19, 2010.
Rappaz, B. et al., "Measurement of the integral refractive index and dynamic cell morphometry of living cells with digital holographic microscopy", Optics Express Opt. Soc. America, vol. 13, No. 23, (Nov. 14, 2005).

(Continued)

*Primary Examiner* — Jonathan Hansen
(74) *Attorney, Agent, or Firm* — Nixon & Vanderhye P.C.

(57) ABSTRACT

Apparatus and method are provided for monitoring and measuring matter and energy fluxes by use of devices able to detect refractive index changes. In one aspect, apparatus use an interference between two electromagnetic radiations in order to provide high sensitivity, enabling fluxes monitoring at the microscopic scale, by measuring phase changes or Optical Path Length (OPL) changes. In one aspect, methods are provided for monitoring and measuring the electrical activity of a biological cells, simultaneously on several cells, without use of electrodes and contrast agents.

18 Claims, 16 Drawing Sheets

(56) References Cited

OTHER PUBLICATIONS

Brazhe, A.R. et al., "Non-invasive study of nerve fibres using laser interference microscopy", Philosophical Transactions of the Royal Society, vol. 366, No. 1880, (Oct. 13, 2008), pp. 3463-3481.

Popescu et al., "Optical imaging of cell mass and growth dynamics", Am J Physiol Cell Physiol, vol. 295, (Jun. 18, 2008), pp. C538-C544).

Rappaz, B. et al., "Simultaneous cell morphometry and refractive index measurement with dual-wavelength digital holographic microscopy and dye-enhanced dispersion of perfusion medium", Optics Letters, vol. 33, No. 7, (Apr. 1, 2008), pp. 744-746.

International Search Report for PCT/IB2010/050747, mailed Aug. 12, 2010.

Brazhe, N.A. et al., "Unraveling Cell Processes: Interference Imaging Interwoven with Data Analysis", Journal of Biological Physics, vol. 32, No. 4, (Nov. 11, 2006), pp. 191-208.

Table 1

| [Cl]$_{intrapip.}$ 44mM | | | | Theo. E$_{cl}$ : -33mV | | | |
|---|---|---|---|---|---|---|---|
| GABA | | | (n = 8) | Muscimol | | | (n = 6) |
| | Equation | R² | E$_{cl}$(mV) | | Equation | R² | E$_{cl}$(mV) |
| Phase | y = -0.1088x - 3.1942 | 0.9461 | -29.4 | Phase | y = -0.1213x - 3.7721 | 0.9429 | -31.1 |
| Current | y = 0.0132x +0.3553 | 0.9371 | -26.9 | Current | y = 0.0163x +0.4411 | 0.9468 | -27.1 |

Table 2

| [Cl]$_{intrapip.}$ 139mM | | | | Theo. E$_{cl}$ : -4mV | | | |
|---|---|---|---|---|---|---|---|
| GABA | | | (n = 5) | Muscimol | | | (n = 5) |
| | Equation | R² | E$_{cl}$(mV) | | Equation | R² | E$_{cl}$(mV) |
| Phase | y = -0.1179x - 0.857 | 0.9229 | -7.3 | Phase | y = -0.1405x - 0.8913 | 0.9614 | -6.1 |
| Current | y = 0.0349x +0.04 | 0.9963 | -2.7 | Current | y = 0.0215x +0.0883 | 0.9881 | -4.1 |

Fig. 16

MONITORING ENERGY AND MATTER FLUXES BY USE OF ELECTROMAGNETIC RADIATIONS

This application is the U.S. national phase of International Application No. PCT/IB2010/050747, filed 19 Feb. 2010, which designated the U.S., and claims priority to IB Application No. PCT/IB2009/050733, filed 24 Feb. 2009, the entire contents of each of which are hereby incorporated by reference.

FIELD OF THE INVENTION

The invention relates to the monitoring and to the measurements of energy and matter fluxes by use of devices using electromagnetic radiations.

BACKGROUND OF THE INVENTION

Movements of matter and energy modify the spatial distributions of these quantities. The present invention uses the fact that such redistributions of energy and matter in space may induce local variations of the electromagnetic (EM) properties. Therefore devices able to probe electromagnetic properties can be used to monitor energy and matter fluxes.

Such type of interactions between EM radiations and matter or energy in movement are commonly used at a large and very large range in astronomy and environmental sciences. For example, the Doppler effect (or Doppler shift) can be used to measure speeds with Light Detection And Ranging (LIDAR) systems. At a smaller range, but still over the centimeter scale, flow meters exist based on optical methods that use Doppler velocimetry, or the Fresnel drag effect, or the property of light scintillation, but such devices requires relatively long probing distances, or even in some cases, the presence of scattering particles in the fluid. The present invention offers solutions to study such type of interactions at a the microscopic scale, thanks to the fact that apparatus according to the present invention measures preferably two type of electromagnetic properties that are highly sensitive to matter and energy densities, even over very short probing distances: the phase shifts of an electromagnetic radiation, and the refractive index.

The present invention will describe in more details an example of application that uses digital holographic microscopy (DHM) to measure ionic currents across the membrane of biological cells. For this particular application, the present invention is based on previous works, see e.g. EP1451646 (Marquet et al.), that have shown that DHM enables to obtain quantitative measurements of the phase shift induced by living cells. For cells, the phase shift can be regarded as a powerful endogenous contrast agent, which contains information about the cell morphology and about intracellular content related to the electromagnetic properties of the cell, in particular refractive index of the cell. The present invention use the fact that temporal variations of the cellular phase shift can be correlated with an electrical activity of cells and describe a method for evaluating associated trans-membrane ionic currents.

For its particular application in the field of cellular trans-membrane ionic currents monitoring, the present invention uses the fact that cellular stimulations inducing ions exchanges (currents) between the intra- and extra-cellular medium, are likely to affect the diffusion of water through the plasma membrane. Therefore changes in intracellular water concentration can be correlated with trans-membrane currents, and as water concentration and refractive index are directly linked, refractive index changes affecting cellular phase shift, can be correlated with ionic currents. Current techniques for online monitoring of this phenomenon (essential to maintain the ionic homeostasis) are scarce. For example, at a macroscopic scale, magnetic resonance imaging (RMI) studies have shown that the diffusion of water in the brain could monitor local increases in neural activity, see e.g. "Direct and fast detection of neuronal activation in the human brain with diffusion MRI" by D. Le Bihan et al, in Proceedings of the National Academy of Sciences of the United States of America 103, pages 8263-8268 in 2006. At the cellular level, imaging techniques based on the transmittance of light (intrinsic signal imaging) have demonstrated that physiological as well as pathological conditions could be associated with changes in cell-volume, see e.g "Optically recorded response of the superficial dorsal horn: dissociation from neuronal activity, sensitivity to formalin-evoked skin nociceptor activation" by J. Lee et al, in Journal of neurophysiology 94, pages 852-864, in 2005. However, all these imaging techniques provide mainly qualitative information on the water flow associated with cell activity. With the present invention the water flow through the cell membrane can be precisely measured with a high sensitivity and a high temporal resolution enabling real-time measurements. From such measurements, ionic currents can be derived very simply and very efficiently.

For its particular application in the field of ionic currents monitoring and measurements, the present invention offers several advantages compared to classical methods of electro-physiology. In particular, the present invention enables to analyze several cells simultaneously (multi-site recording) with a single detector (e.g. a video camera), while standard methods requires costly and complex instrumentations involving several electrodes. In addition, the present invention enables to measure currents in a non-invasive way without electrodes. Moreover, the present invention enable to determine unambiguously the direction of ionic fluxes, providing a clear differentiation between inward and outward currents, while electro-physiology fails in determining if an outward current is due to an outflow of cations (e.g. $K^+$), or to an inflow of anions (e.g. $Cl^-$), and inversely if an inward current is due to an inflow of cations, or to an outflow of anions.

Compared to optical electrophysiological techniques that use molecules capable of emitting light in response to their electrical environment, such as voltage sensitive dyes and fluoresceing proteins, the present invention offers the great advantage that bioelectric activity can be probed without use of contrast agents. Moreover, the present invention is directly sensitive to currents, while actual optical electrophysiological techniques are mainly voltage sensitive. In addition the present invention can be used to monitor optically electrical activities involving ions species for which no reliable optical dyes exist at present, such as chloride ions, which are of particular interest since they have important physiological roles, for instance in the central nervous system.

OBJECTIVES OF THE INVENTION

The present invention aims at providing an apparatus and a method for monitoring and measuring energy and matter fluxes by use of electro-magnetic radiations. In a preferred embodiment, such an apparatus comprise a device able to detect a phase shift on electromagnetic radiations crossing a portion of space where an energy or matter flux arises. In another preferred embodiment such an apparatus comprise a device able to detect permettivity including dielectric constant and refractive index changes in a portion of space where an energy or matter flux arises.

Another objective is to provide apparatus and method for monitoring or measuring currents, including ionic currents, through the membrane of biological cells without electrodes and without contrast agents, at several locations within a cell, or on several different cells simultaneously, and providing a clear differentiation between inward and outward currents. It is also an objective of the present invention to provide an apparatus and method for measuring or monitoring matter exchanges trough the biological membrane of cells, said matter exchanges comprising, among others, water exchanges. Finally, it is also an objective of the present invention to provide an apparatus and method for measuring optically electrical activities involving ions for which no optical dyes exist, such as chloride ions.

SUMMARY OF THE INVENTION

In many case, energy or matter fluxes modify locally the speed of propagation of electromagnetic radiations. In other words, we can also say that a modification of the spatial distribution of matter or energy induce a modification of the spatial distribution of the index of refraction. Therefore, as stated by the present invention, devices able to detect refractive index changes, or speed of propagation changes, can be used to study energy and matter fluxes.

Among devices able to detect refractive index changes, those which are sensitive to the phase of electromagnetic radiations are particularly interesting for monitoring fluxes at the microscopic scale and we can mention those using the well known principles of: interferometry, holography, digital or numerical holography, quantitative phase microscopy, Hilbert phase microscopy, differential interference contrast, classical phase contrast, defocusing methods, or optical tomography.

The present invention will describe in more details the use of digital holographic microscopy (DHM) to monitor and to measure ionic currents, and watter exchanges across the membrane of biological cells, but the present invention is not restricted to this particular case. It is obvious that fluxes others than ions and water, across other membranes than cell membranes, or in environments without membranes, can be monitored or measured with the present invention. As well, others methods than DHM can be used by the present invention, as long as they are sensitive to changes of electromagnetic properties associated to matter or energy fluxes.

SHORT DESCRIPTION OF THE DRAWINGS

Figure 4:
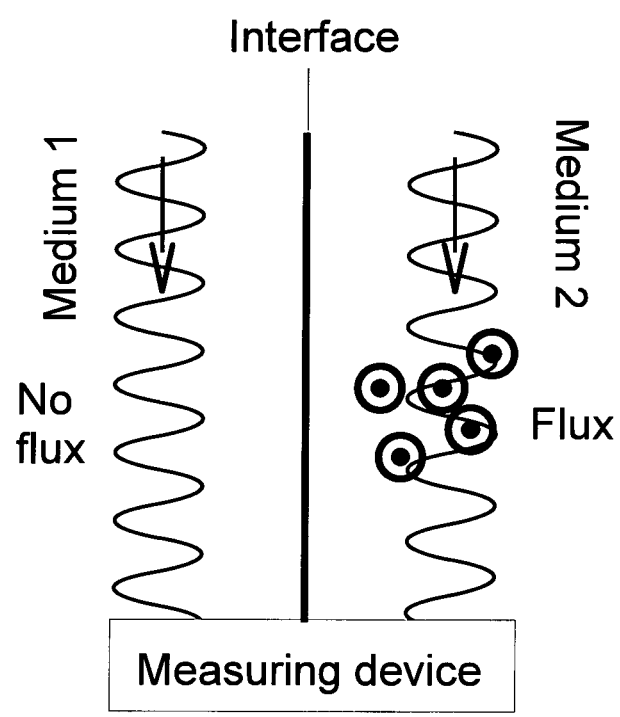

FIG. 4 illustrates a scheme of a particular configuration involving a fluxes that can be monitor with an apparatus and method according to the present invention. The configuration comprise an interface separating medium 1 and medium 2. A flux is present only in medium 2 (presented here perpendicular to the plane of the page), and medium 1 may serve to extract baseline signals.

Figure 5:
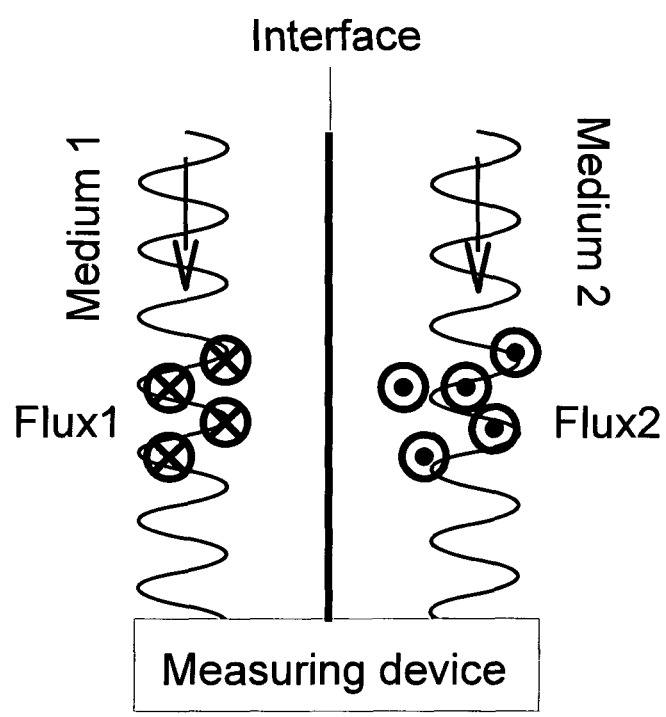

FIG. 5 illustrates a scheme of a particular configuration involving fluxes that can be monitor with an apparatus and method according to the present invention. The configuration comprise an interface separating medium 1 and medium 2. Fluxes are present in medium 1 and medium 2 (presented here perpendicular to the plane of the page).

Figure 6:
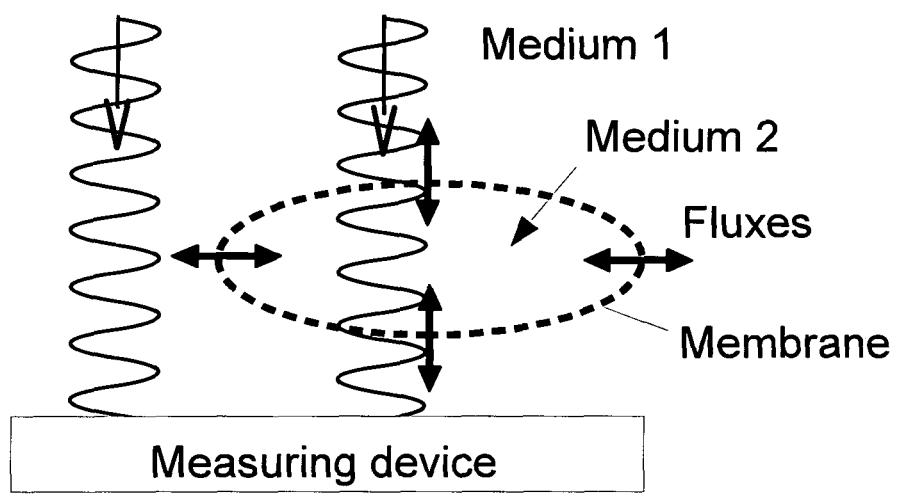

FIG. 6 illustrates a scheme of a particular configuration involving fluxes that can be monitor with an apparatus and method according to the present invention. The configuration comprise a semipermeable membrane enclosing medium 2 immersed in medium 1.

Figure 7:
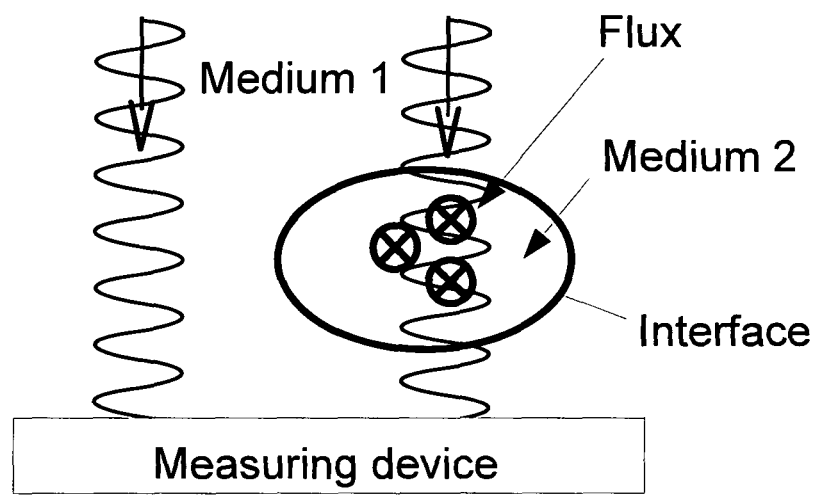

FIG. 7 illustrates a scheme of a particular configuration involving fluxes that can be monitor with an apparatus and method according to the present invention. The configuration comprise an interface enclosing medium 2 immersed in medium 1.

Figure 8:
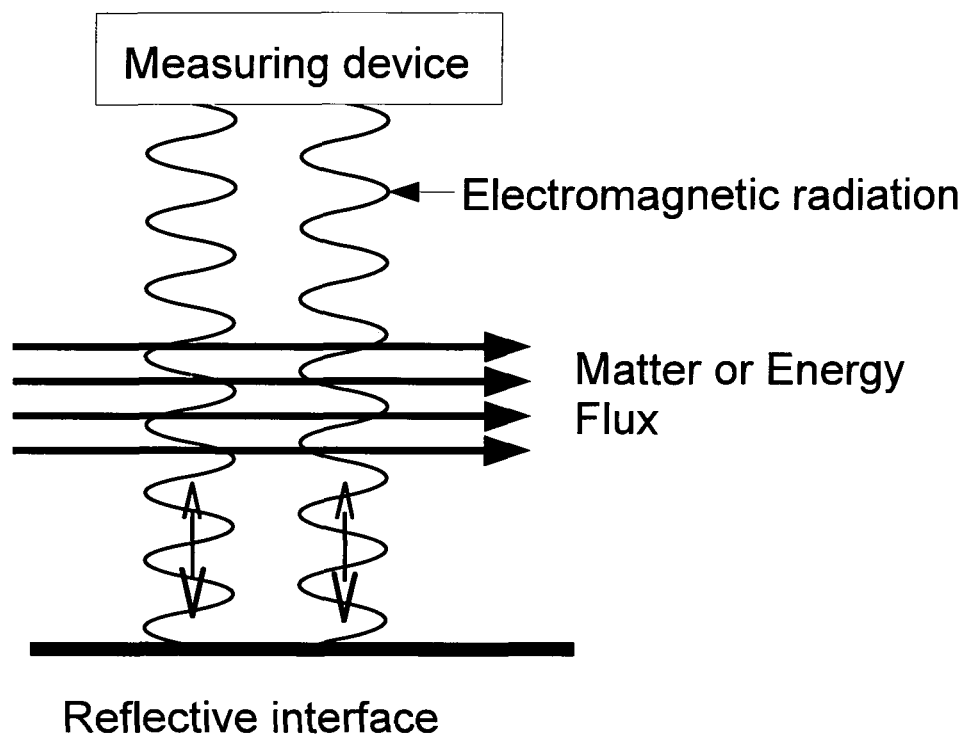

FIG. 8 illustrates a scheme showing that the present invention can be used to monitor fluxes in a so-called reflection configuration.

Figure 9:
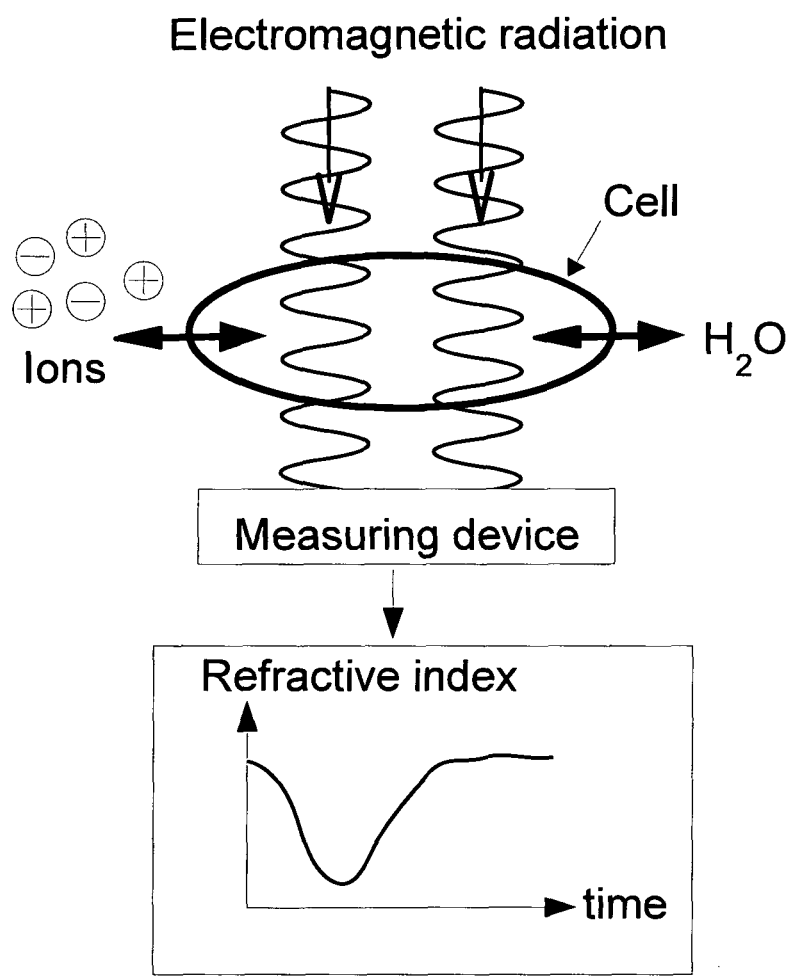

FIG. 9 illustrates a scheme showing that the present invention can be used to monitor ionic currents and water fluxes crossing the membrane of a biological cell by measuring temporal variations of the refractive index of the cell.

Figure 10:
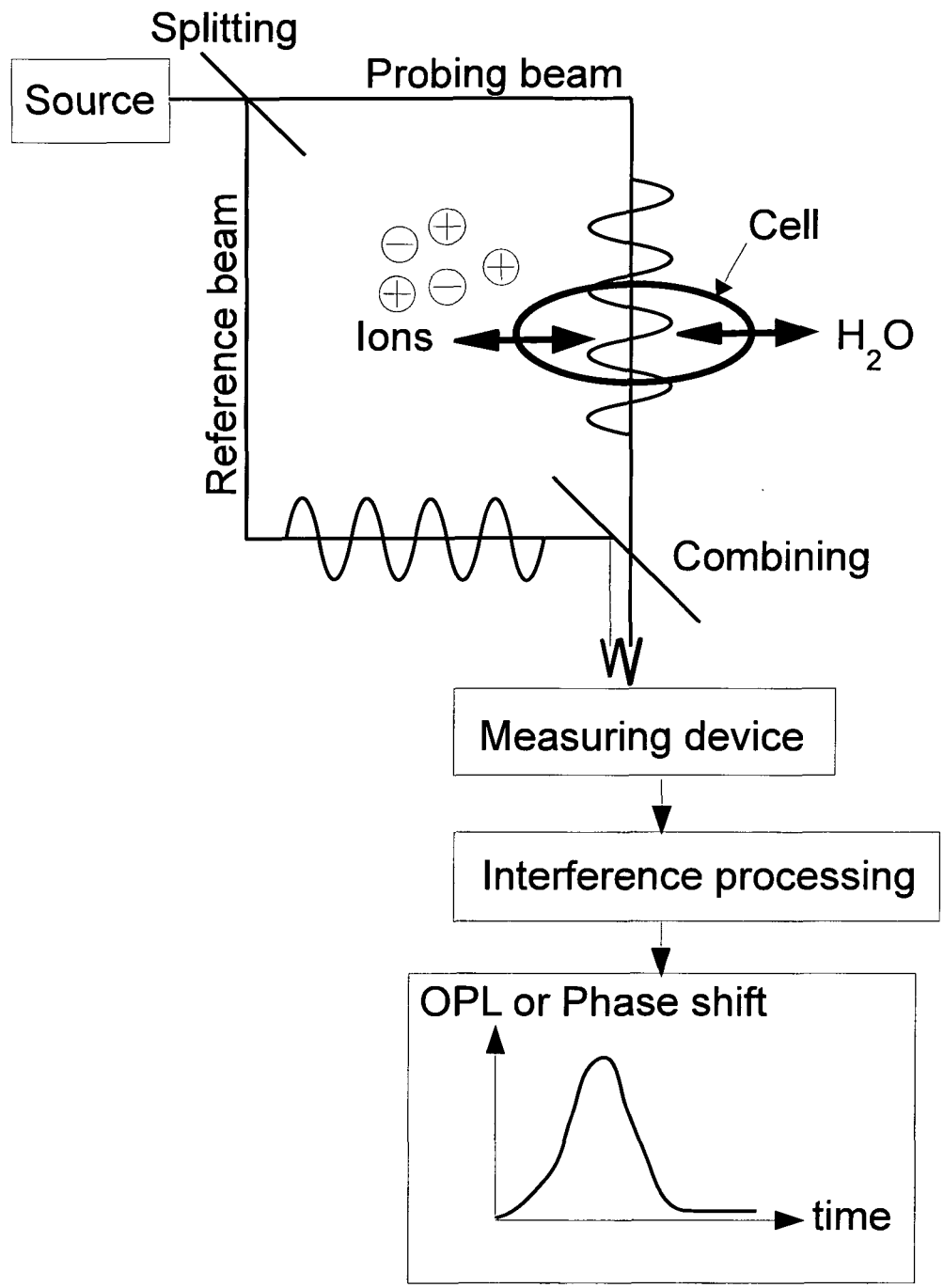

FIG. 10 illustrates a scheme showing that the present invention can be used to monitor ionic currents and water fluxes crossing the membrane of a biological cell by measuring temporal variations of the Optical Path Length (OPL) or temporal variations of the phase shift. According to a preferred embodiment, the OPL or the Phase are obtained by use of an interference between a probing beam and a reference beam.

Figure 11:
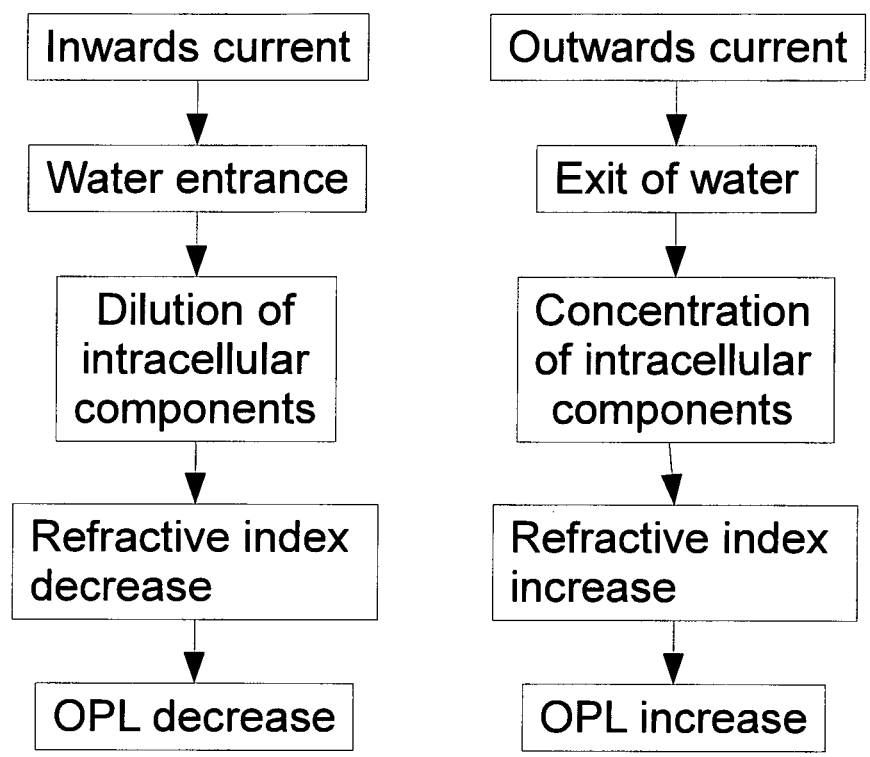

FIG. 11 compares the variations of water flows, intracellular components concentration, refractive index, and Optical Path Length (OPL) for inwards and outwards trans-membrane cellular ionic currents monitored according to the present invention.

Figure 12:
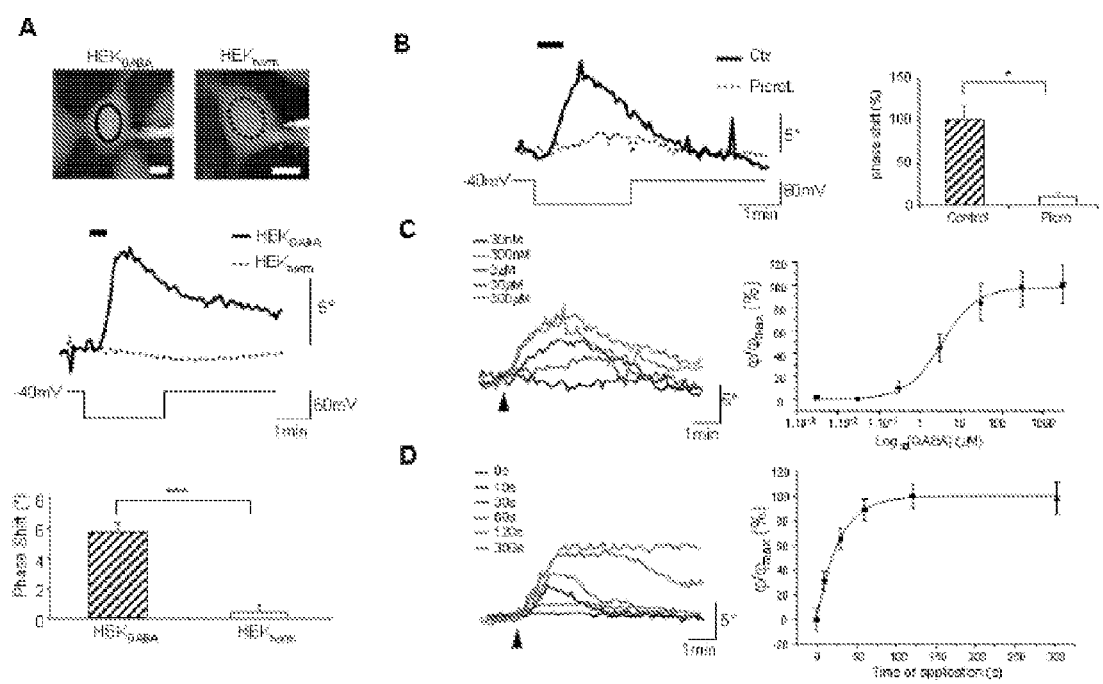

FIG. 12 Phase shift is associated with activation of $GABA_A$ receptors expressed in $HEK_{GABA}$ A: (Top) Phase image of patched $HEK_{GABA}$ (left) and $HEK_{norm}$ (right) recorded by DHM. The full ($HEK_{GABA}$) or the dotted ($HEK_{norm}$) ovals in the middle of the cells correspond to the region of interest (ROI) where the phase signal is recorded. (Middle) Application of GABA (3 µM, 30 s; bar) during a pulse of voltage (from −40 mV to −100 mV; 2.5 min) triggered a strong transient increase of the phase signal in $HEK_{GABA}$, but was ineffective in $HEK_{norm}$. (lower trace) The Bar chart shows the difference between $HEK_{GABA}$ (n=15) and $HEK_{norm}$ (n=10) in response to application of GABA at −100 mV.

B: At −100 mV, in presence of picrotoxin (Picrot., 30 µM), application of GABA (3 µM, 30 s; bar) reduces the phase shift (dotted line) when compared to control conditions (Ctr; full line). The Bar chart shows the difference between Picrotoxin (picro) and Control condition (n=13) in response to application of GABA at −100 mV.

C: (Left) Example of traces of phase shift obtained after the successive application of GABA (from 30 nM to 3 mM, 30 s; arrow head,) to the same $HEK_{GABA}$ at −100 mV. With the increase in GABA concentration, the phase shift increased until it reached a plateau. (Right) The graph reports this effect for 6 cells at a holding potential of −100 mV. The curve shown was the best fit of the data to the logistic equation described in the METHODS section. Fitting the data to the logistic equation yielded an $EC_{50}$ of 3.4 µM.

D: (Left) Example of traces of phase shift obtained after the successive application of GABA (3 µM, 30 s; arrow head) to the same $HEK_{GABA}$ at −100 mV. With the increase in application time of GABA, the phase shift increased until it reached a plateau. (Right) The graph reports this effect for 9 cells at holding potential of −100 mV. The curve was obtained using a logistic fit with an $T_{1/2}$ of 19.4 s.

Figure 13:
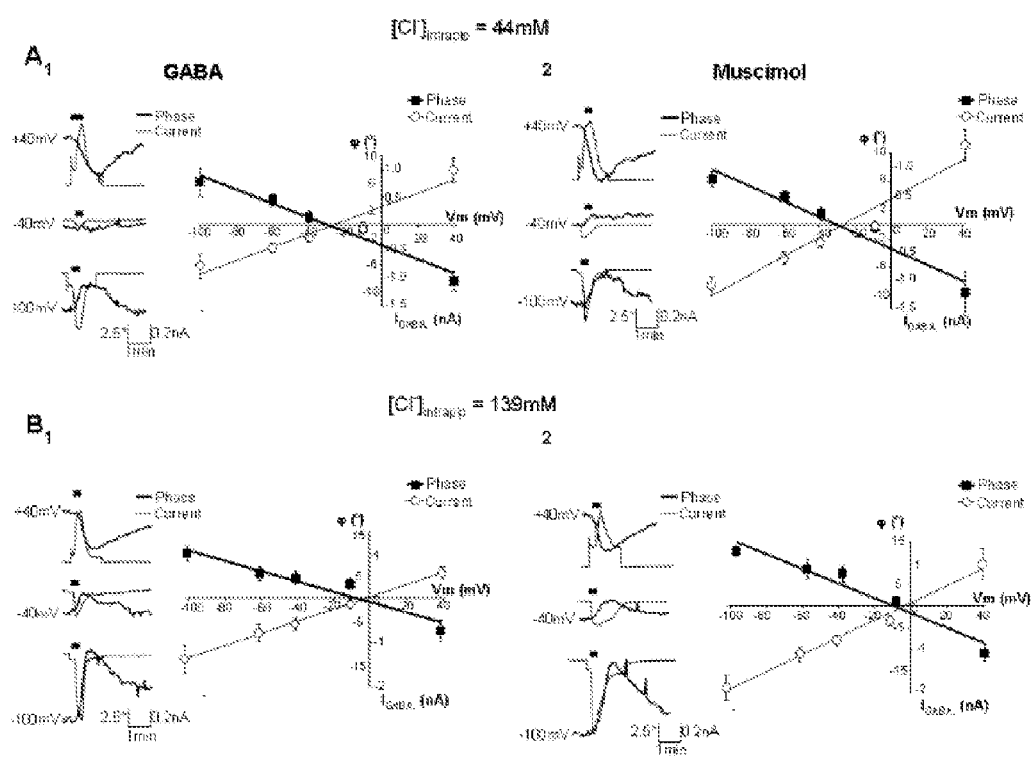

FIG. 13 Determination of the value of the reversal potential for Cl from the phase shift evoked by GABA or muscimol application.

$A_1$: (left) Example of 3 simultaneous traces of current (dotted line) and phase shift (thick line) recorded with 40 mM of $[Cl^-]_{intrapip}$ on the same $HEK_{GABA}$. At −100 mV, application of GABA (3 µM, 30 s) triggered a inward current concomitantly to an increase in the phase signal. Conversely, at +40 mV, same applications of GABA triggered an outward current accompanied by a decrease of the phase signal. Note that for −40 mV (close to the resting potential for Cl), the current and the phase shift were very small. (Right) The ϕ/V curve (full square and thick line) and the I/V curve (empty circle and thin line) obtained with GABA (n=8) indicated an $E_{Cl}$ of −27 mV and −29 mV respectively (see also Table 1).

$A_2$: With an application of the $GABA_A$ agonist muscimol (1 µM, 30 s, M), the data were similar to those obtained with GABA. With Muscimol, the $E_{Cl}$ was −32 mV with the ϕ/V curve and −27 mV with the I/V curve (n=6; see also Table 1).

$B_1$ and $B_2$: (left) In the presence of 139 mM of $[Cl^-]_{intrapip}$, traces of current and phase shift obtained after application of GABA (3 µM, 30 s; G) ($B_1$) or Muscimol (1 µM, 30 s, M) ($B_2$) were similar, except for −40 mV, where a larger current and phase shift were detected compared with 40 mM of $[Cl^-]_{intrapip}$. In this condition, the value of $E_{Cl}$ was shifted to a more positive value. (Right) The ϕ/V curve (full square and thick line) and the I/V curve (empty circle and thin line) obtained with GABA (n=5) indicated $E_{Cl}$ of −7 mV and −3 mV, while with muscimol (n=5), $E_{Cl}$ were −4 mV (ϕ/V curve) and −4 mV (I/V curve) (see also Table 2).

Figure 14:
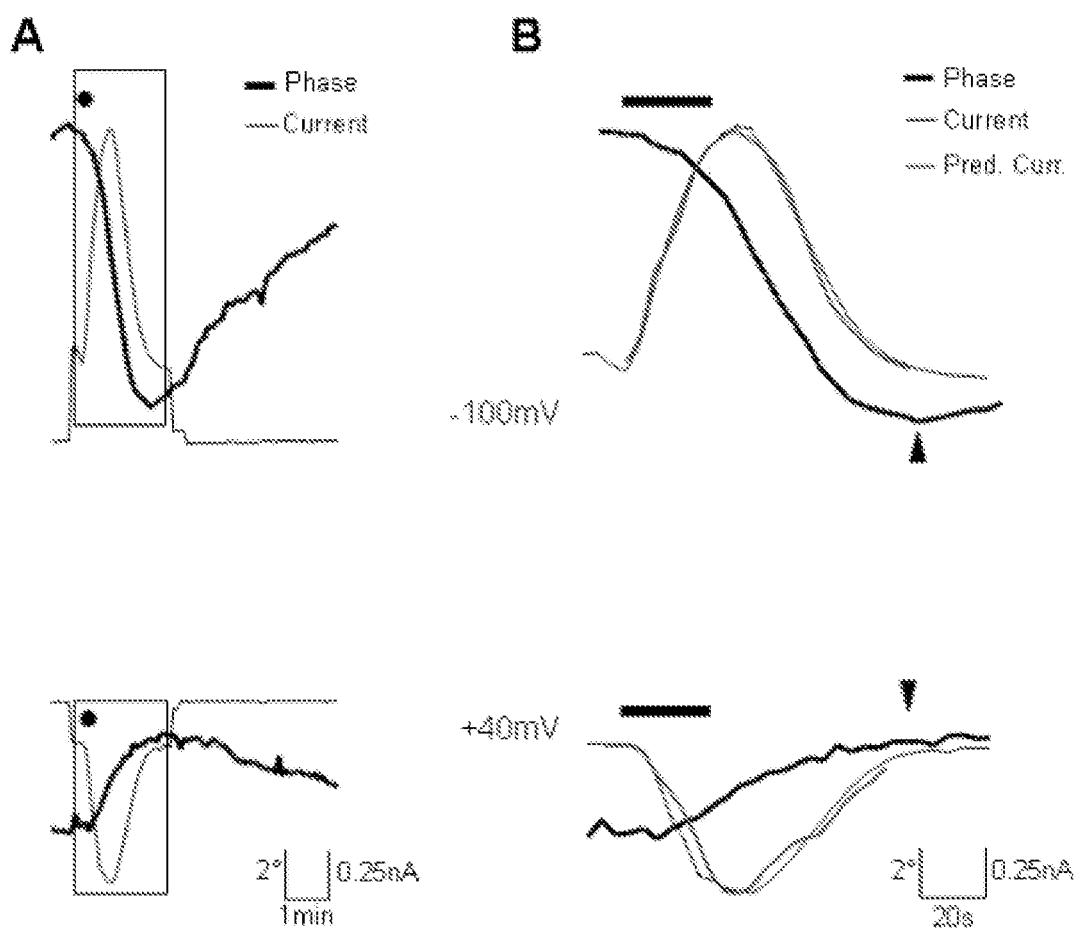

FIG. 14 The $GABA_A$ gated current can be determined from the phase signal by a simple mathematical relation.

A: Simultaneous traces of current (thin line) and phase signal (thick line) obtained after application of GABA (3 µM; 30 s; dot) for 2 different membrane potentials (top: −100 mV; below: +40 mV). Each trace of current and phase signal corresponds to an average of 6 individual current or phase shift from 6 $HEK_{GABA}$ cells.

B: Expansion of traces visualized in A (parts defined by rectangles). For each level of membrane potential, the peak of phase shift (indicated by the arrow head) was reached when the $I_{GABA}$ was terminated. According to equation 6 the phase signal can predict the current (Pred. Curr.: red line) superimposed to the recorded current.

Figure 15:
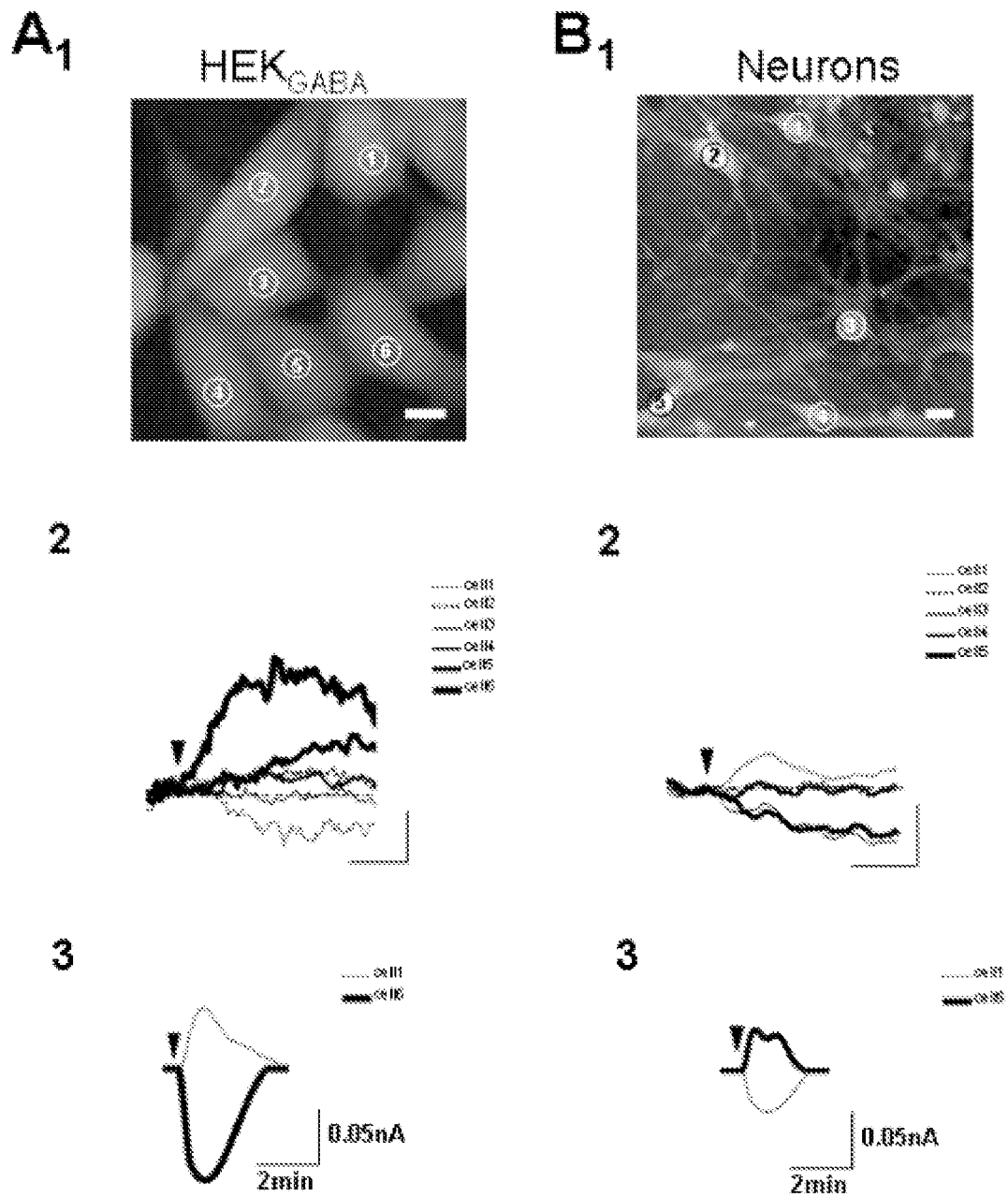

FIG. 15 Non invasive multi recording of $Cl^-$ flux from several cells (Top): Representative phase images of $HEK_{GABA}$ cells (A1) and cultured cortical neurones (B1) visualized in DHM (scale bar: 10 µm). (Middle): Traces of phase signal recorded from corresponding cells showed above. For $HEK_{GABA}$ cells (left), application of GABA (3 µM, 30 s) triggers an increase in the phase signal for cells 2, 4, 5 & 6, while for cell 1 a decrease in the optical signal is observed. Note that for cell 3, there is no detectable optical signal. For neurons (right), application of GABA (100 µM, 30 s) triggers a decrease in phase signal for cells 3 & 5 while, GABA evoked a small increase in the phase signal for cell 1 and no detectable optical signal for cells 2 & 4. (Bottom): Determination of the predicted current for $HEK_{GABA}$ 1 & 6 (left) and from neurones 1 and 5 (right) according to the equation 6.

FIG. 16 Table 1: Determination of $E_{Cl}$ with a $[Cl^-]_{intrapip}$ of 44 mM. Table 2: Determination of $E_{Cl}$ with a $[Cl^-]_{intrapip}$ of 139 mM.

DESCRIPTION OF THE INVENTION

Fluxes Monitoring by Measurement of Refractive Index

The physical principle governing the present invention is the fact that energy or matter fluxes may modify locally the speed of propagation of electromagnetic radiations, because this speed of propagation is straightly linked to the density of matter and to the density of energy. In other words and equivalently, we can also say that a modification of the spatial distribution of matter or energy induce a modification of the spatial distribution of the index of refraction. Therefore, as stated by the present invention, devices able to detect refractive index changes, or speed of propagation changes, can be used to study energy and matter fluxes. Among such devices, we can mention those based on the principles of refractometry, reflectometry, ellipsometry, spectroscopic ellipsometry, imaging ellipsometry or time of flight measurements.

Figure 1:
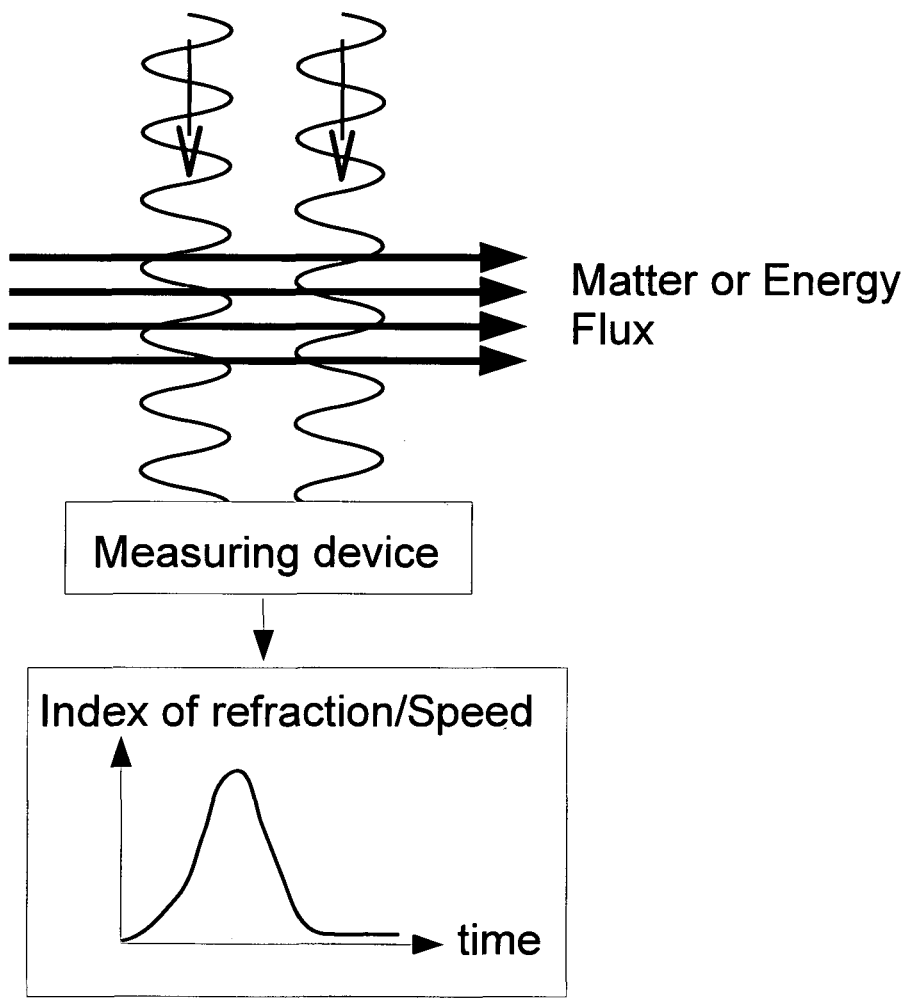
FIG. 1 illustrates a scheme of an apparatus according to the present invention. A measuring device provides the index of refraction as a function of time and enables to monitor a flux of matter or energy, which has been crossed by an electromagnetic radiation.

FIG. 1 present a schematic view of an apparatus according to the present invention in its most basic form. A measuring device providing the index of refraction or the speed of propagation as a function of time enables to monitor a flux of matter or energy. In this general case, an apparatus according to the present invention may incorporate a source generating the EM radiation, or this radiation may originate from another source located outside the apparatus. The corresponding apparatus comprise at least one detector sensitive to electromagnetic radiations, connected to a device able to provide a measurement of the index of refraction. For example, the apparatus according to the present invention may comprises a time of flight camera, a reflectometer, an ellipsometer, an imaging ellipsometer or a refractometer such as: a digital refractometer, a laboratory or Abbe refractometer, an inline process refractometer or a Rayleigh refractometer.

Fluxes Monitoring by Phase Measurements

Among devices able to detect an interaction between an EM radiation and a flux of matter or energy, those which are sensitive to the phase of electromagnetic radiations are particularly well adapted to monitor flows and fluxes at a short range, down to the microscopic scale, since they are highly sensitive to refractive index changes. Among such devices, we can mention those using the principles of: wavefront sensing, Hartmann-Shack wavefront sensing, interferometry, interference microscopy, shearing interferometry, lateral shearing interferometry, 4-wave lateral shearing interferometry, phase-shifting interferometry, holography, digital or numerical holography, digital holographic microscopy, quantitative phase imaging, quantitative phase microscopy, phase reconstruction by use of the transport of intensity equation, Fourier phase microscopy, Hilbert phase microscopy, Diffraction Phase Microscopy or tomography, heterodyne Mach-Zehnder phase microscopy.

To clarify links between a flux of energy and matter, the refractive index and the phase, we can summarize things as follows:
The refractive index is an electromagnetic property of a medium, and the presence of a flux of matter or energy may modify the refractive index of the medium.
The phase is a parameter describing and EM radiation, and the phase is sensitive to refractive index changes.

Therefore a flux modifying the refractive index of a medium will in turn modify the phase of an EM radiation probing the medium.

We can also add the fact that in what follows, the phase will be sometimes introduced trough the concept of Optical Path length (OPL) that establishes a link between the phase ($\phi$) and the refractive index (n): $\phi=2\pi \cdot OPL/\lambda=2\pi \cdot n \cdot h/\lambda$, where $\lambda$ is the wavelength of the EM radiation, and h the distance probed by an EM radiation in a medium of refractive index n.

Figure 2:
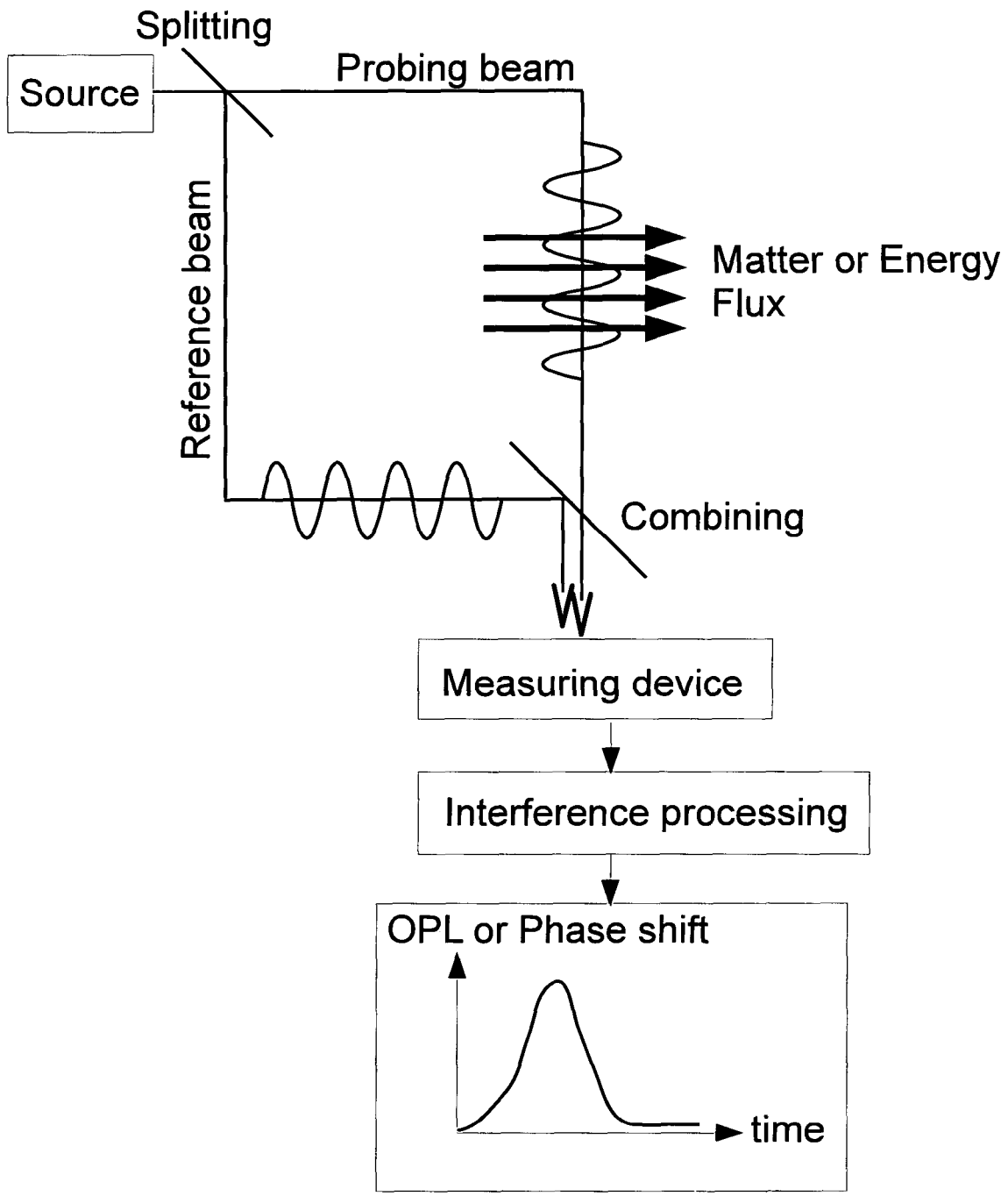
FIG. 2 illustrates a scheme of an apparatus according to the present invention that monitor a flux of energy or matter by providing temporal measurements of Optical Path Length (OPL) or the Phase. According to a preferred embodiment, the OPL or the Phase are obtained by use of an interference between a probing beam and a reference beam.

In one preferred embodiment presented in FIG. 2, the apparatus according to the present invention makes use of an interference between two EM radiations: A probing beam interacting with an energy of matter flux (probing beam), and a reference beam that do not interact with the flux. In this case, the apparatus comprises:

- At least on source of EM radiation, for example a light source such as a laser, a laser diode, a light emitting diode.
- Means for splitting the emitted radiation into two parts: a probing beam and a reference beam. For example a beam splitter or a fiber coupler.
- Means for combining the reference beam and the probing beam after splitting and after interaction of the probing beam with an energy or matter flux. For example a beam splitter or a fiber coupler.
- Means for detecting the interference between the probing beam and the reference beam. For example an optical sensor, such as photo-diode or a CCD camera.
- Means for processing the detected interference in order to provide and Optical Path Length (OPL), or an optical phase, or a phase shift. For example, a method for interferogram analysis as used in classical interferometry, or a method for numerical reconstruction of digital holograms as used in Digital Holographic Microscopy, or a method for quantitative phase contrast imaging.

Additionally apparatus according to FIG. 2 may comprise several elements such as:

- Microscope objectives for magnifying the portion of space probed by the probing beam, and if necessary associated optical elements such as a tube lens.
- Optical elements such as mirrors, lenses, polarizing optics, optical filters, wave-plates or spatial filters to adapt the shape of beams to the experimental configuration.
- Means for combining the reference and probing beams in order to create an off-axis interference on a camera in order to provide an off-axis hologram.
- Means for tuning the wavelength of the electromagnetic radiation emitted by the source in order to enable spectroscopic measurements.
- Means for tuning the wavelength of the electromagnetic radiation emitted by the source in order to optimize the signal, for example by approaching region of the electromagnetic spectrum where refractive index changes are amplified by a resonances (for example absorption peaks).
- Means for adding at least one sources of EM radiations, for example sources emitting at different wavelengths.
- Means for adding at least one reference beam and/or at least one probing beam.

Combination of the Present Invention with Other Methods

Apparatus and method according to the present invention can be easily implemented in instrumentations providing several measurements or imaging possibilities in parallel. In particular, the present invention can be used in combination with classical electro-physiological techniques or with classical microscopy techniques, such as fluorescence microscopy, confocal microscopy, or phase contrast microscopy.

Examples of Configurations for Fluxes Measurement and Monitoring

Apparatus and method according to the present invention can be used to study energy or matter fluxes of any types in solids, liquids and gazes, without restrictions regarding fluxe directions or substrates or containing devices. There are however some specific configurations presenting a particular interest for practical applications as presented in FIGS. 3 to 7.

Figure 3:
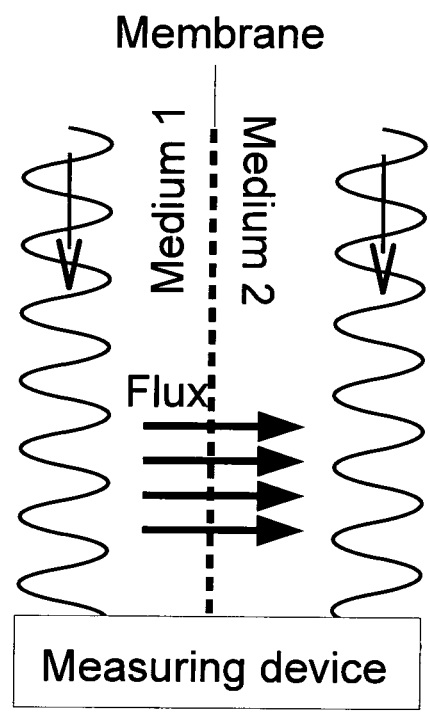
FIG. 3 illustrates a scheme of a particular configuration involving fluxes that can be monitor with an apparatus and method according to the present invention. The configuration comprise a semipermeable membrane crossed by the flux.

For example, as presented in FIG. 3, the present invention can be used to monitor fluxes crossing a semipermeable membrane. In this case, comparing the signals measured from both sides of the membrane can be useful to monitor or to measure fluxes by considering the relative variations of refractive index, or phase, or phase shift, or OPL between medium 1 and medium 2. By extension, configurations with several membranes separating several media can also be considered.

For example, as presented in FIG. 4, the present invention can be used to monitor a flux (presented as perpendicular to the plane of the sheet in FIG. 4) by comparing two measurements: A first one measured in a region with a flux (medium 2), and a second one in a region without flux (medium 1). With this configuration, the measurement in the region without flux in medium 1 provide kind of a baseline which can be used as a reference to evaluate what is specifically due the presence of a flux in medium 2. Medium 1 and medium 2 can be different or similar. Medium 1 and medium 2 can be separated by a physical interface or not. Medium 1 and medium 2 can be close together or not. This configuration may correspond to practical situations in the field of microfluidics.

By extension of the configuration of FIG. 4, and as shown in FIG. 5, medium 1 may also have a flux. In this case, comparing the signals measured from medium 1 and medium 2 can be useful to monitor or to measure fluxes by considering the relative variations of refractive index, or phase, or phase shift, or OPL between medium 1 and medium 2.

For example, as presented in FIG. 6, the present invention can be used to monitor fluxes crossing a closed semipermeable membrane separating a medium 2 immersed or enclosed in medium 1. In this case, regions exist where medium 1 only is probed, and other regions exist where medium 2 and medium 1 are probed. Comparing the signals measured from these two types of regions can be useful to monitor or to measure fluxes by considering the relative variations of refractive index, or phase, or phase shift, or OPL. By extension, configurations with several closed membranes separating several media can also be considered. A particular case of this configuration, of particular interest regarding applications of the present invention is a biological cell immersed in a liquid solution.

For example, as presented in FIG. 7, the present invention can be used to monitor fluxes in a medium 2 that is immersed or enclosed in a medium 1. With this configuration, measurements in regions with medium 1 only provide kind of a baseline which can be used as a reference to evaluate what is specifically due the presence of a flux in medium 2. Medium 1 and medium 2 can be different or similar. Medium 1 and medium 2 can be separated by a physical interface or not. This configuration may correspond to practical situations in the field of fluidics, microfluidics, and nanofluidics.

As presented in FIG. 8, configurations described in FIGS. 3 to 7, and more generally all configurations incorporating fluxes, can also be probed in a so-called reflection configuration, with a reflective interface making EM radiations traveling back and forth trough fluxes. Configurations using multiple reflection can also be used to increase the probing distance.

Quantitative Estimation of Fluxes—Relationship Between Fluxes and Refractive Index Changes Fluxes monitoring by the present invention is straightforward since temporal signals revealing variations of refractive index can be directly interpreted as an evidence of the fact that fluxes have occurred in the probed region of space. It is exactly the same for phase changes or OPL changes, since these quantities depends essentially, as the refractive index, on the speed of propagation of electromagnetic radiations. In what follows, refractive index, or its symbol n, OPL and phase or phase shifts will be used indifferently.

However converting refractive index changes in quantitatively reliable matter or energy fluxes is more difficult because the relationships between the refractive index and the density of matter or energy depends on several parameters among which we find: the wavelength of the EM radiation, its polarization, the temperature and the pressure. In addition and generally expressed, at the atomic or molecular level, the refractive index depends on the relative permittivity and permeability, which describes how electric and magnetic fields affects, and are affected by, a medium crossed by an EM radiation. Several models exist that aim at describing or approximating the dielectric properties of materials and media but a general formulation cannot be given here since it depends always on parameters, and on approximations or hypothesis that are specific to the measurement configuration.

However, as a refractive index is linked to a density of matter or energy, and as flux is generally defined as an amount that flows through a unit area per unit of time, we can generally conclude that a flux will be proportional to the first temporal derivative of the measured signal (refractive index, phase, or OPL). As well, as the link between OPL (or phase) and refractive index depends on the probing distance, models for fluxes estimation based on OPL measurements, will have to take into account spatial parameters describing the measurement configuration, such as diameters, thickness or volumes. In the following sections one of such models is given to describe the measurement of cellular ionic currents by the present invention.

Application to the Measurement of Cellular Transmembrane Ionic Currents

FIG. 9 presents schematically an application of the present invention for monitoring and measuring the electrical activity of biological living cells. Basically, the measurement principle is the following:

A trans-membrane inonic current is accompanied by a flow of water trough the cell membrane. If ions enter into the cell (inwards current), water enter into the cell. If ions go out of the cell (outwards current), water go out of the cell.

Water flows induced by ionic currents dilute or concentrate the intracellular contents. An entrance of water dilutes the intracellular contents. An exit of water concentrates the intracellular contents.

Dilutions or concentrations of intracellular contents modify the refractive index of the cell, which decreases in case of water entrance, and which increases in case of water exit.

In summary, it results that:

Ionic currents traveling inside a cell (inwards currents) decrease the refractive index of the cell.

Ionic currents traveling outside a cell (outwards currents) increase the refractive index of the cell.

This simple rule establishes the fact that refractive index measurements can be used to monitor ions exchanges between a cell and its surroundings. Cell to cell exchanges, as well as cell to external medium exchanges can be studied this way.

As already mentioned, among techniques available for measuring refractive index changes, those which are sensitive to the phase of EM radiations are well adapted to study microscopic specimen, such as cells, since the phase of a radiation is a parameter that is highly sensitive to refractive index, even over very short probing distances. In a preferred embodiment presented in FIG. 10, phase measurements on biological cells can be achieved by use of a device recording and processing the interference between a reference beam and a probing beam.

The relationship between the refractive index of a cell ($n_c$), and the phase shift $\phi$, implies the cellular Optical Path Length (OPLc) and is given by:

$$\phi = 2\lambda \cdot OPLc/\lambda = 2\pi \cdot (n_c - n_m) h / \lambda \quad (1),$$

where $\lambda$ is the wavelength of the radiation, h is the cell thickness at the measurement point, and $n_m$ the refractive index of the medium inside which the cell is immersed. From equation (1), and from the general dependency of ionic currents to cellular refractive index, it results that:

Ionic currents traveling inside a cell (inwards currents) decrease the cellular OPL or phase shift.

Ionic currents traveling outside a cell (outwards currents) increase the cellular OPL or phase shift.

FIG. 11 summarizes the principle that governs ionic currents monitoring according to the present invention by comparing the general behaviors for inwards and outwards currents in terms of water flows, intracellular contents concentrations, refractive index changes and OPL changes. We precise that OPL measurements are not required if devices enable to measure directly the refractive index.

Measurement of Cellular Transmembrane Ionic Currents: Influence of Volume Changes There general rules described above give clear and simple relationships for monitoring ionic currents by the present invention. However if an apparatus according to the present invention uses OPL or phase shifts measurements, the interpretation of the measurements may have to take into account the fact that, depending on situations, the measured signals may also depend on variations of the cell thickness h, as stated by equation (1). Therefore, cellular volume changes may also contribute to the measured signal.

In particular, water flows induced by ionic currents may directly contribute and may, in most cases, reduce the current related OPL changes. For example, if we consider an inwards current, the water entrance will decrease the refractive index but may also increase the average cell thickness, and in turn the cell volume. To separate the influences of refractive index and volume (or thickness), decoupling procedures can be applied. Such type of decoupling procedures use two measurements at different wavelengths, possibly simultaneously as described in EP1451646 (Marquet et al.), or two sequential measurements in two different perfusion solutions of different refractive index and identical osmolarity, as describe by Rappaz et al. "Measurement of the integral refractive index and dynamic cell morphometry of living cells with digital holographic microscopy", in Optics Express 13, 9361-9373 (2005). In principle, actual knowledges indicate that refractive index changes are significantly higher than volume changes for most cellular activities.

Processes of cell volume regulation may also bring a contributions to the OPL signal. In particular, cell volume regulation processes may follow water flows induced by ionic currents. However, the kinetics of such processes is rather slow and their effects on OPL measurements can be dissociated from the kinetics of current-induced OPL by simply decomposing the period of measurements into two steps First a short term response, with a rapid variation of OPL that is directly correlated to a trans-membrane current and that involves mainly refractive index variations.

And directly after, or possibly slightly delayed, a slower OPL variation due to a volume regulation process during which the cell retrieves its initial volume (approximately the volume of the cell before electrical activity).

Model for Determining Trans-Membrane Inonic Currents from Phase Measurements

In this section, we describe how the determination of the phase signal changes—reflecting cellular volume (V) variations as well as cellular index of refraction ($n_c$) modifications—can be used to calculate the associated ionic current (I). To address this question we posited two hypotheses. First, we postulated that the $n_c$ value depends linearly on the concentration of the different intracellular components. Second, it is reasonable to assume that the volume variations induced by the water movement accompanying the ionic movements are proportional to the number of ions having passed through the membrane through channels.

By defining the volume factor $\beta=V(t)/V_0$ as the ratio between the cell volume measured during ionic current at a time t and the initial cell volume $V_0$ before ionic current, these two hypotheses allow to write:

$$n_c(t) \approx \frac{[C_0]}{\beta(t)^s} \quad (2)$$

$$\beta(t) = \frac{\varepsilon \int_0^t I dt + \Delta V + V_0}{V_0} \quad (3)$$

where $n_c(t)$ is the refractive index at time t, $[C_0]$ represents the concentration of the different intracellular components ionic current [mM/ml], I the instantaneous current [C/s] and $\in$ a constant representing the volume variation associated with the net charge movement through the cell membrane [ml/C]. $\Delta V$ represents non-electrogenic cell volume changes except those directly related to a trans-membranar net charge movement. Concretely the quantity $\Delta V$ can include simple electrically neutral ion transport systems as well as more complex processes involved in the cell volume regulation. The parameter s has been introduced to take into account cell processes inducing volume variations leading to refractive index changes by mechanisms other than dilution or concentration of the intracellular content by ions and water fluxes. Practically, s $\in$[0,1], s=1 corresponding to a simple dilution or concentration of the cell content.

Finally, according to equations (1), (2), (3) and considering the relation between cell thickness and cell volume variations which can be described as:

$$\beta^r(t) = \frac{h(t)}{h_0} \quad (4)$$

where $h_0$ is the cell thickness before current and r a parameter related to the cell deformation along the z-axis associated with the volume variation, we can obtain:

$$I(t) = \frac{V_0}{\varepsilon} \frac{d}{dt}\left(\frac{\varphi_0}{\varphi(t)}\right)^{1/s-r} - \frac{1}{\varepsilon}\frac{d\Delta V(t)}{dt} \quad (5)$$

Thus, equation (5) establishes a clear relationship between the phase signal φ(t) and the current I(t). If we further assume that the slow variations of cell volume $\Delta V(t)$ can be neglected, for instance if we restrict the phase signal analysis to a short time period, equation (5) can be simplified:

$$I(t) = \frac{V_0}{\varepsilon} \frac{d}{dt}\left(\frac{\varphi_0}{\varphi(t)}\right)^{1/s-r} \quad (6)$$

Example of Application: Optical Recording of Chloride Current by Digital Holographic Microscopy In the next sections we describe in details a particular application of the present invention that make use of a Digital Holographic Microscope (DHM), to record optically chloride currents in two different types of cells: HEK cells and neurons. This application is described here for illustrative reasons only and do not represent a restriction to potential applications of the present invention, and to the different forms of apparatus and methods according to the present invention.

Optical Recording of Chloride Current by DHM: Abstract

Digital Holographic Microscopy (DHM) is a non invasive optical imaging technique able to provide quantitative phase images of individual living cells. The phase signal largely depends on the intracellular refractive index. We detected a phase shift in the optical signal after application of GABA on $GABA_A$ receptor-expressing HEK cells. This effect is blocked by Picrotoxin and mimicked by Muscimol. Furthermore, the value for the reversal potential of chloride obtained by establishing phase/voltage relations is superimposable to that obtained by voltage/current relations and dependent on the intracellular concentration of chloride, thus affording an optical method to visualize chloride fluxes. Based on these observations, we developed an algorithm that allows to derive the amplitude of the $GABA_A$ receptor-dependent current from the phase shift determined by DHM. Furthermore such chloride currents can be determined from the DHM signal simultaneously in several cells in the same culture of HEK cells as well as primary neurons. These results illustrate the use of DHM to determine non invasively and simultaneously in several cells ionotropic receptor-mediated currents.

Optical Recording of Chloride Current by DHM: Introduction

Cell-to-cell communication mediated by signalling molecules such as hormones or neurotransmitters acting at specific receptors triggers short-term responses which result in changes in ionic permeabilities, affecting membrane potential and excitability, as well in activation of intracellular signalling cascades. Some of these signalling mechanisms, particularly those involving changes in ionic permeability, are likely to affect the diffusion of water (constituting up to 70% of cell mass) through the plasma membrane. Current techniques for online monitoring this phenomenon (essential to maintain the ionic homeostasis) are scarce. For example, at a macroscopic scale, functional magnetic resonance imaging (fRMI) studies have shown that the diffusion of water in the brain could monitor local increases in neural activity. At the cellular level, imaging techniques based on the transmittance of light (intrinsic signal imaging) have demonstrated that physiological as well as pathological conditions could be associated with changes in cell-volume. However, all these imaging techniques provide mainly qualitative information on the water flow associated with neuronal activity at the cellular level.

Recently, significant progress has been made in Quantitative Phase Microscopy (QPM) techniques that enable to obtain full-field quantitative phase imaging of transparent living cells, allowing to visualize cell structure and dynamics. In contrast to the non-invasive phase contrast (PhC), initially proposed by F. Zernike and by Nomarski's differential interference contrast (DIC), which provide qualitative information about cell structure, QPM, provides a quantitative measurement of the phase shift induced by a transparent specimen on the transmitted wavefront. The phase shift, or the optical path difference (OPD) containing considerable information about the cell morphology as well as intracellular content related to the refractive index properties, can be regarded as a powerful endogenous contrast agent. Bilbiographic data about QPM can be found in: Curl, C. L. et al, "Quantitative phase microscopy: A new tool for investigating the structure and function of unstained live cells", Clin Exp Pharmacol P 31, 896-901 (2004). Marquet et al "Digital holographic microscopy: a noninvasive contrast imaging technique allowing quantitative visualization of living cells with subwavelength axial accuracy", Opt Lett 30, 468-470 (2005). Popescu, G. et al "Diffraction phase microscopy for quantifying cell structure and dynamics" Opt Lett 31, 775-777 (2006). The QPM that we will use here, called digital holographic microcopy (DHM), has the ability to explore cell dynamics by providing, from a single recorded hologram, quantitative phase images of a living cell with a nanometric axial sensitivity (see Rappaz B. et al. "Measurement of the integral refractive index and dynamic cell morphometry of living cells with digital holographic microscopy. Optics Express 13, 9361-9373 (2005)). Practically, an original numerical processing of holograms (see for example EP1119798, and EP1910996) allows not only to calculate the phase shift but also to reconstruct the whole wavefront diffracted by the specimen and consequently to compensate for aberration and experimental noise (time drift, vibration, defocusing, etc.) thus ensuring a high phase stability making possible to explore biological processes across a wide range of time scales, from milliseconds to hours.

For each pixel of the DHM images, the phase shift is given by equation (1), which establish the fact that the phase signal depends on two distinct cell parameters: h which provides information concerning cell morphology and volume, and $n_c$ whose value is related to the amount of non-aqueous material present in the cell and is essentially determined by the protein content (see Barer, R. "Determination of dry mass, thickness, solid and water concentration in living cells", Nature 172, 1097-1098 (1953)).

DHM can therefore quantitatively detect small variations of the phase, which mainly depend on the refractive index of the cell ($n_c$) and cell morphology and volume (h). We previously determined that the value of the phase is largely dependent on the refractive index rather than on cell morphology (Rappaz B. et al. "Measurement of the integral refractive index and dynamic cell morphometry of living cells with digital holographic microscopy. Optics Express 13, 9361-9373 (2005)). In turn, this refractive index is dependent on the protein concentration of the cell (Popescu, G., et al "Optical imaging of cell mass and growth dynamics", American journal of physiology 295, C538-544 (2008)). Accordingly, entry of water will dilute the intracellular protein content resulting in a decrease in the phase, while an exit of water will concentrate the protein content leading to an increase in the phase.

Given the possibility afforded by DHM to monitor the influence of transmembrane water fluxes on the intracellular refractive index, we reasoned that it could be possible to monitor water fluxes associated with transmembrane ionic fluxes mediated by agonist-activated receptor-gated channels or by transporters specific for a given ionic species. To this end, initial experiments aiming at monitoring the DHM phase signal induced by a specific ion-selective ligand-gated channel have been performed; for this purpose we undertook the study of $GABA_A$ chloride selective receptors expressed in HEK293 cells.

In this highly selective system we found that GABA produces a receptor-specific optical signal detectable by DHM. The reversal potential for Cl− as determined by DHM is similar to that determined by conventional electrophysiological techniques. In addition, a simple mathematical analysis of the phase response determined by DHM can predict the chloride transmembrane current, providing the opportunity to quantitatively measure currents without any electrode.

Finally, another feature of DHM revealed by this study is the possibility to achieve current determinations in several cells simultaneously, as the optical signal can be acquired instantaneously from any cell in the field of the objective. Such multisite Cl− fluxes were determined in HEK cell expressing GABA receptors as well as in cortical neurones in culture.

Optical Recording of Chloride Current by DHM: Material and Methods

Cell Preparations:

$HEK_{GABA}$ cells: HEK 293 cells stably expressing configurations of rat $GABA_A$ receptors ($HEK_{GABA}$) were generously given by Hoffmann-LaRoche (Basel, Switzerland). Briefly, cDNAs encoding rat $GABA_A$ α1, β2 and γ2s subunits were subcloned into the expression vectors pIRESpuro2, pIRESneo2 and pIREShygro2 vectors (Clontech, Mountain View, Calif.), respectively. The pIRES/$GABA_A$ α1, β2, γ2s, constructs were sequenced to confirm their nucleotide sequence and then cotransfected into HEK 293 cells at a ratio of 1:1:2 (plasmid mass ratio) using the lipofectamine 2000 kit according to the manufacturer's instructions (Invitrogen, Carlsbad, Calif., USA). Transfected cells were grown in minimal essential medium (Invitrogen) supplemented with 10% fetal calf serum (Invitrogen), 20 mM HEPES (Invitrogen) and 100 U/ml penicillin/100 μg/ml streptomycin (Invitrogen) for 48 hours and then, the cells were transferred to the selection medium containing 0.3 μg/ml puromycin (Clontech, Mountain View, Calif., USA), 300 μg/ml hygromycin B (Roche Diagnostics, Mannheim, Germany) and 200 μg/ml G418 (Invitrogen) for the generation of stable cell lines. Cell colonies were isolated and expression of the $GABA_A$ α1β2γ2s receptor was determined by [$^3$H] flumazenil binding.

Neuronal cell cultures: Primary cultures of cortical neurons were prepared from E17 OF1 mice embryos. Briefly, embryos were decapitated and brains removed and placed in PBS-glucose. Cortex was removed under a dissecting microscope and collected in a small Petri dish in PBS-glucose. Cell dissociation was obtained by gentle trituration with a fire-polished Pasteur pipette in Neurobasal medium supplemented with B27 and GlutaMAX (Invitrogen). Cells were plated at an average density of 15000 cells/cm$^2$ in supplemented Neurobasal medium on poly-ornithine coated glass coverslips (20 mm Ø). After 3-4 h, coverslips were transferred to dishes containing glial cell monolayers in supplemented Neurobasal medium. Neurons were maintained at 37° C. in a humidified atmosphere of 95% air/5% $CO_2$ and were used after 21-35 days in vitro (DIV).

Electrophysiology recording: All cultures were perfused in an artificial cerebrospinal fluid (ACSF) containing (in mM): NaCl 150, KCl 3, D-glucose, 10 HEPES 10, CaCl$_2$ 3, and mM MgCl$_2$. 2 (pH 7.4; Room temperature). For some experiments performed on HEK cells, picrotoxin (30 µM, Tocris) was added to the ACSF. GABA (3 µM, Tocris), Muscimol (1 µM, Tocris) were dissolved in ACSF and applied by bath perfusion (for 0 s to 300 s). Whole-cell recordings were made, and signals were amplified by using Multiclamp 700B amplifiers (Axon Instruments, Union City, Calif.) and digitized by means of an ITC-1600 interface (Instrutech, Great Neck, N.Y.) to a PC computer running Igor Pro (Wavemetrics, Portland, Oreg.). All currents (sampling interval, 5 kHz) were low-pass filtered (2 kHz). They were recorded with pipettes containing 95 mM potassium-gluconate, 40 mM KCl, 10 mM Hepes, 2 mM MgCl$_2$ (pH 7.3). For some experiments, 95 mM potassium-gluconate was substituted with 95 mM KCl to reach a final concentration of [Cl$^-$]$_{intrapip}$, to 139 mM. The pipettes were pulled with a DMZ universal puller.

Imaging: Holograms are acquired with a DHMT 1000 (Lyncée Tech SA, PSE-EPFL). A laser diode produces the coherent light (λ=683 nm) which is divided by a beam splitter into a reference wave and an object wave. The object wave diffracted by the specimen is collected by a microscope objective and interferes with a reference beam to produce the hologram recorded by the CCD camera. Frequency of hologram acquisition is 0.2 Hz. Reconstruction of the original image from the hologram is numerically achieved by a computer. The reconstruction algorithm provides simultaneous amplitude and quantitative phase images of the cells (Koala software). It is important to note that an extensive quality control of the DHM technique has been published by Rappaz et al "Comparative study of human erythrocytes by digital holographic microscopy, confocal microscopy, and impedance volume analyzer" Cytom Part A 73A, 895-903 (2008). GABA was added after a minimum of 1 min of stable baseline recording for both the optical and the electrical signals.

Offline analysis: The electrophysiological and optical recordings were analysed by using MATLAB 7.6 (Mathworks Software, Natick, Mass.) and all curves have been fitted by using ORIGIN 7.5 (Microcal Software, Northampton, Mass.). GABA concentration-response (or time application-response) profiles were fitted to the following logistic equation: $\phi/\phi_{max}=1/[1+(EC50/[GABA])^n]$, where $\phi$ and $\phi_{max}$ represented the normalized GABA induced phase shift at a given concentration (or time application) and the maximum phase shift induced by a saturating [GABA], EC50 was the half-maximal effective GABA concentration (or time application), and n was the slope factor. For both, optical and electrical response of GABA application, rise time ($\tau_{rise}$) and decay time ($\tau_{decay}$) correspond to 0-100% peak amplitude. All data are presented as means±SEM. Student's t-test (paired or unpaired) to determine statistical significance (p<0.05).

Optical Recording of Chloride Current by DHM: Results

For all experiments, the transfected HEK cells (HEK$_{GABA}$) cultures had a cell density such that HEK$_{GABA}$ were in contact with neighbouring cells (at least 60% of confluency). Their morphologies were identical to those of the non-transfected HEKs (HEK$_{norm}$) namely polygonal in shape (FIG. 12). In terms of electrical properties, HEK$_{GABA}$ had a resting potential of −30.8±0.8 mV (range: −20 to −45 mV; n=63) and an input resistance of 233±13 M Ω. (Range: 150 to 500 M Ω). There were no significant differences in terms of electrical properties between HEK$_{GABA}$ and HEK$_{norm}$ ($V_m$: −34.6±1.7 mV; p>0.05; R$_{inp}$: 214±36; p>0.05; n=10).

GABA Triggers a Phase Shift in the Optical Signal in HEK$_{GABA}$

At −100 mV, bath perfusion of GABA (3 µM, 30 s) on HEK$_{GABA}$ led to a transient increase of phase signal (Δϕ=5.46±1.38°; n=15), while a similar application of GABA had no effect on HEK$_{norm}$ (Δϕ=0.33±0.55°; n=6; p<0.005) (FIG. 12). In the presence of a GABA$_A$ receptor antagonist, picrotoxin (30 µM), the phase response evoked by GABA application was significantly reduced (−82±17%, p<0.05, n=10) (FIG. 12), while the specific agonist, muscimol (1 µM; 30 s, n=6) mimicked the effect of GABA (FIG. 13). All results indicate that the optical signal obtained after application of GABA was associated with the activation of GABA$_A$ receptors expressed in HEK$_{GABA}$. Finally, the amplitude of the phase shift depended both on the concentration of GABA (EC$_{50}$=3.4 µm) and the length of application (t$_{1/2}$=19.4 s) (FIG. 12).

Determination of the Reversal Potential of Cl$^-$ by DHM

Through the patch pipette, different membrane potentials were imposed. For a given cell, at −100 mV, the application of GABA resulted in a transient increase of phase signal (Δϕ=6.43±2.02°; n=7) as described above (FIG. 13). In contrast, at +40 mV, GABA triggered a transient strong decrease of phase signal (Δϕ=−8.14±1.47; n=8) (FIG. 13). In reporting the maximal amplitude of the phase shift as a function of the membrane potential, we obtained a relationship which we called "Phase/Voltage" (ϕ/V), in analogy with the "current/voltage" relationship (I/V). In doing so, we were able to determine the reversal potential of the ion involved, here Cl$^-$ ($E_{Cl}$), in this case −29 mV (FIG. 13; table 1 in FIG. 16). This value was close not only to the theoretical value of $E_{cl}$ ($E_{Cl(Th)}$=−33 mV) calculated with the Nernst equation using values taken from our experimental conditions (table 1 in FIG. 16), but also to that obtained by classical electrophysiology with the I/V curve (−27 mV; FIG. 13; table 1). To confirm that changes in phase signal were associated with the flow of Cl$^-$, we modified the concentration of this anion in the patch pipette ([Cl$^-$]$_{intrapip}$.) from 44 mM to 139 mM. Accordingly, the values of the reversal potential for Cl$^-$ obtained with the ϕ/V and I/V relationships were shifted to less negative values (respectively −7 mV and −3 mV; n=5) and were similar to the value of $E_{Cl(Th)}$ calculated under these new conditions (−4 mV) (table 2 in FIG. 16; FIG. 13).

Finally, similar results were obtained with the specific GABA$_A$ receptor agonist, muscimol (1 µM, 30 s). The ϕ/V relationship established a reversal potential of −31 mV with a [Cl$^-$]$_{intrapip}$. of 40 mM (n=6) (FIG. 13 and table 2 in FIG. 16) while with a [Cl$^-$]$_{intrapip}$. of 139 mM (n=5), the reversal potential was around −6 mV (FIG. 13 and table 2 in FIG. 16), thus confirming that the Cl$^-$ flow was due to the opening of the conductance of GABA$_A$ receptors.

These results clearly show that the electrochemical properties of a given ionic conductance (here the conductance for Cl$^-$) can be determined by DHM with the same precision as that achieved with classical electrophysiological approaches.

The GABA$_A$ Receptor-Mediated Current can be Derived (I$_{GABA}$) from the DHM Signal Our experimental recordings showed that, while the two types of signals (electrical and optical) provide the same information on GABA$_A$ receptor properties, their kinetics are strikingly different (FIGS. 13 and 14). Thus, at −100 mV, the rise time ($\tau_{rise}$) or decay time ($\tau_{decay}$) of the phase shift ($\tau_{rise}$: 85.0±9.3 s; $\tau_{decay}$: 243±20.2 s, n=8) was significantly longer than for the I$_{GABA}$ ($\tau_{rise}$: 23.9±2.3 s; p<0.005; $\tau_{decay}$: 47.8±4.7 s; p<0.005). Similarly, at +40 mV, the kinetic constants were also significantly longer for the phase shift ($\tau_{rise}$: 92.5±15.3 s; $\tau_{decay}$: 220±19.0 s) than for I$_{GABA}$ ($\tau_{rise}$:

29.3±1.6 s; p<0.05; $\tau_{decay}$: 57.2±1.3 s; p<0.005 n=6). These measures of kinetics suggest nevertheless a strong relationship between the current and phase signal generated by GABA where the current is a parameter representing a number of charges per unit of time and the phase signal would be a mirror of the accumulation of these same charges during the total opening time of the conductance.

As presented previously, this relationship between the current (here $I_{GABA}$) and the DHM phase signal ($\phi_t$) is explicitly given by equation 5. However, for the typical GABA applications considered in this work (no longer than a few tens of seconds), the corresponding phase response can be decomposed into two components, a rapid one accompanying $I_{GABA}$ and a delayed one corresponding generally to a phase recovery while $I_{GABA}=0$. In addition, the two components are separated by a phase plateau behaviour indicating that the non-electrogenic volume variation $\Delta V$ can also be decomposed into two components, a rapid ($\Delta V_r$) and a delayed ($\Delta V_d$) one, which do not overlap and thus are likely to result from different underlying mechanisms. Consequently, only the rapid phase response involving $\Delta V_r$ had been used to calculate the $I_{GABA}$ and the Equation 5 can be rewritten as followed $$I_{GABA}(t) = \frac{V_0}{\varepsilon^*_{GABA}} \frac{d}{dt}\left(\frac{\varphi_0}{\varphi(t)}\right)^{1/s-r} \quad (7)$$

where $\in^*_{GABA}$, formerly defined as $$\varepsilon^*_{GABA}(t) = \varepsilon_{GABA} \frac{V_0 \frac{d}{dt}\left(\frac{\varphi_0}{\varphi(t)}\right)^{1/s-r}}{V_0 \frac{d}{dt}\left(\frac{\varphi_0}{\varphi(t)}\right)^{1/s-r} - \frac{d\Delta V_r}{dt}},$$

represents the effective volume variations per number of net charges transported through the membrane. This relation takes into account any volume variations, including the non-electrogenic ones ($\Delta V_r$)

In order to quantitatively derive $I_{GABA}$ from the rapid phase response, several parameters from equation 7 must be known. Practically, $V_0$ as well as the parameters r and s have been measured by the decoupling procedure (see Rappaz et al "Measurement of the integral refractive index and dynamic cell morphometry of living cells with digital holographic microscopy" Optics Express 13, 9361-9373 (2005)). Consequently, a single parameter remains to be determined, namely $\in^*_{GABA}$, to calculate the current. Practically, as far as the rapid phase is considered, the decoupling procedure has allowed to demonstrate that value of s is not statistically different from 1 in HEK cells and, indicating that the intracellular refractive index varies directly in proportion to cell volume changes. Interestingly, the typical values of the parameter r are within the range 0.5-0.8 (HEK cell as well as in neurons) reflecting the fact that the cell deformation associated with the volume change is not isotropic (r=0.33) but preferentially along the z-axis.

FIG. 14 shows examples of currents derived from the phase signal at two different holding potentials (−100 and +40 mV) as calculated with equation 7. For these calculations, the parameter $\in^*_{GABA}$ in equation 7, was computed by performing a least squares fit, in order to minimize the sum of the square of the deviations between the measured current from the phase derived current ($I_{pred}$). It must be stressed that the adjustment of this single parameter $\in^*_{GABA}$ allows to obtain a $I_{pred.}$ in very good agreement with the measured current.

Typical values for the parameters $\in^*_{GABA}$ lie within the range of 90-110 μm³/nC for HEK cell and 60-120 μm³/nC for neurons.

Measurement of Simultaneous Cl⁻ Currents in Different Cells

Results presented so far, clearly showing that the phase shift signal can be used to quantitatively monitor an ionic flux, namely Cl⁻ flux, were obtained in cells with the membrane potential clamped at different values in order to vary the electrochemical gradients driving Cl⁻ fluxes and the resulting currents. In order to fully take advantage of the possibility afforded by DHM to derive currents from an optical signal, we have determined phase-derived currents simultaneously in several unpatched cells. These multisite measurements were performed both in HEK cells and in neurones.

In $HEK_{GABA}$ cells, application of GABA (3 μM, 30 s) induces three types of phase responses in different cells of the same culture (FIG. 15A): an increase in the phase signal (5.5+/−1.6°, n=6), a decrease (−2.9+/−0.6°, n=6) or no detectable changes (0.06+/−0.35°, n=15). These heterogeneous responses result from the fact that the resting potential varies from cell to cell ranging from −20 to −45 mV, with a mean value of −31 mV, n=63, thus a potential very close to the reversal potential of Cl⁻ (around −30 mV; table 1 in FIG. 16). This is consistent with the fact that over 50% of the cells exhibit a modest or no detectable phase signal. Nevertheless, from the simultaneous measurement of the phase responses, the $GABA_A$ receptor-mediated Cl⁻ current could be determined simultaneously in several unpatched cells (FIG. 15).

Having demonstrated the ability of DHM to determine $GABA_A$-receptor-mediated Cl-currents simultaneously in several cells specifically overexpressing $GABA_A$ receptors, we wanted to test the possibility that such measurements could also be performed in neurons. To this end, we applied of GABA (100 μM, 30 s) to unpatched cortical neurons in primary culture and observed optical responses in several cells within the same culture (FIG. 15B). Neurons also presented heterogeneous phase responses. Thus out of 46 neurons, GABA triggered a decrease of phase signal in 13 cells (−2.55+/−0.29°, an increase in 3 cells (1.16+/−0.47°) and a modest or no detectable signal in 30 cells (−0.16+/−0.2°). Similar results were obtained with local and shorter GABA applications. As for $HEK_{GABA}$, the neuronal resting potential (−57 mV, n=26) is rather close to the reversal potential of Cl⁻ (−70 mV). The Cl⁻ current generated by GABA in different neurons, could be derived from the optical signal (FIG. 15B3). These results indicate that DHM affords the possibility to determine Cl⁻ currents simultaneously in several cells in a non-invasive way, without the use of electrodes or fluorescent dyes.

Optical Recording of Chloride Current by DHM: Discussion

Results reported in this article demonstrate that DHM is a simple and reliable optical technique to study the pharmacological properties of an ionic conductance with a precision comparable to that achieved with conventional electrophysiological techniques. Moreover, with an appropriate mathematical treatment, the ionic current generating the phase shift can be derived from the optical signal. This provides the opportunity to simultaneously determine in several cells, an ionic current without recording electrodes.

Thus, the first series of results obtained with DHM show that the optical signals are specifically linked to the activation of $GABA_A$ receptors expressed by $HEK_{GABA}$ (no optical response on $HEK_{norm}$), with pharmacological characteristics typical of those of $GABA_A$ receptors. The ionic species underlying the GABA current could be determined by constructing a phase/current plot and determine a reversal potential, which was close to the theoretically-determined equilibrium potential of chloride. This is particularly interesting for chloride, since no reliable optical imaging techniques are available. Indeed, DHM produces an optical signal without using a fluorescent dye or a contrast agent. The optical signal obtained is an intrinsic one, linked to a physiological process. The illumination system used for DHM is rather conventional (laser diode) and of low power (~200 μW/cm$^2$). To the best of our knowledge this is the first example of an optical technique providing without dye, precise information on specific ionic fluxes in a quantitative manner comparable to that obtainable by electrophysiology.

Some additional points deserve discussion as they reveal some unexpected features of DHM. Thus an outward current as determined electrophysiologically may be due to the outflow of a cation, e.g. K$^+$, or the inflow of an anion, e.g. Cl$^-$. Interestingly, with DHM, the actual direction of the ionic flow, entry or exit from the cell, can be determined. Thus, by coupling electrophysiology with DHM the ionic nature of an outward current can unambiguously be determined.

More importantly, a simple mathematical expression, with a single unknown parameter $\in^*_{GABA}$ and relating the phase shift to the measured current has been derived and successfully applied to provide a quantitative determination of the ionic current from the DHM optical signal. Practically, we showed that the rapid part of the phase shift was strictly dependent on the current $I_{GABA}$. We have also demonstrated that it was possible to derive a current from the analysis of this rapid part of the phase signal by using equation 7 with $\in^*_{GABA}$ fixed at a constant value. The parameter $\in^*_{GABA}$ takes into account volume variation from various origins, including the non-electrogenic ones ($\Delta V_r$) in addition to those directly related to the number of net transported charge. It is therefore likely that $\Delta V_r$ does not significantly contribute to the rapid phase response considering that $\Delta V_r$=0 just before the GABA application. Concerning the delayed part of the optical response, it starts immediately after the end of $I_{GABA}$ and corresponds to the return of the phase signal to its initial level. The decoupling procedure (see Supplementary information II) that we have applied allowed us to determine that the second phase of the optical signal corresponds to a reestablishment of V, and is therefore linked to counter-regulatory processes of volume regulation. Moreover, the kinetic analysis indicated that this process has a rather slow time constant ($\tau_{decay}$>200 s). Several membrane proteins may be involved in volume regulation such as those operating Volume-Regulated-Anion Channel (Helix, N. et al. "Inhibition of the endogenous volume-regulated anion channel (VRAC) in HEK293 cells by acidic diaryl-ureas" The Journal of membrane biology 196, 83-94 (2003)), or ionic co-transporters (Gillen, C. M. & Forbush, B., 3rd. "Functional interaction of the K-Cl cotransporter (KCC1) with the Na-K-Cl cotransporter in HEK-293 cells" The American journal of physiology 276, C328-336 (1999)) and aquaporins (Heo, J., Meng, F. & Hua, S. Z. "Contribution of aquaporins to cellular water transport observed by a microfluidic cell volume sensor" Analytical chemistry 80, 6974-6980 (2008)).

Finally, we have shown that DHM allows to monitor in a non-invasive manner (without patch electrode and/or dye) $I_{GABA}$ simultaneously in several cells within the same preparation.

In conclusion, this study describes a novel application of DHM to study at the single-cell level non-invasively and without the use of dyes, the optical signature of a specific receptor activity, in this case the GABA$_A$ receptor selectively permeable to Cl$^-$. In addition, appropriate mathematical treatment of the optical signal affords the possibility to quantitatively determine the dynamics of the current triggered by the receptor activity. Finally DHM allows to perform simultaneous multi-cell current recordings.

REFERENCES

Patents
EP1119798
EP1910996
EP1451646
Other publications
Darquie, A., Poline, J. B., Poupon, C., Saint-Jalmes, H. & Le Bihan, D. Transient decrease in water diffusion observed in human occipital cortex during visual stimulation. Proceedings of the National Academy of Sciences of the United States of America 98, 9391-9395 (2001).
Le Bihan, D., Urayama, S., Aso, T., Hanakawa, T. & Fukuyama, H. Direct and fast detection of neuronal activation in the human brain with diffusion MRI. Proceedings of the National Academy of Sciences of the United States of America 103, 8263-8268 (2006).
Andrew, R. D. & MacVicar, B. A. Imaging cell volume changes and neuronal excitation in the hippocampal slice. Neuroscience 62, 371-383 (1994).
Isokawa, M. Altered pattern of light transmittance and resistance to AMPA induced swelling in the dentate gyrus of the epileptic hippocampus. Hippocampus 10, 663-672 (2000).
Lee, J., Tommerdahl, M., Favorov, O. V. & Whitsel, B. L. Optically recorded response of the superficial dorsal horn: dissociation from neuronal activity, sensitivity to formalin-evoked skin nociceptor activation. Journal of neurophysiology 94, 852-864 (2005).
Carl, D., Kemper, B., Wernicke, G. & von Bally, G. Parameter-optimized digital holographic microscope for high-resolution living-cell analysis. Applied optics 43, 6536-6544 (2004).
Curl, C. L., Bellair, C. J., Harris, P. J., Allman, B. E., Roberts, A., Nugent, K. A. & Delbridge, L. M. D. Quantitative phase microscopy: A new tool for investigating the structure and function of unstained live cells. Clin Exp Pharmacol P 31, 896-901 (2004).
Marquet, P., Rappz, B., Magistretti, P. J., Cuche, E., Emery, Y., Colomb, T. & Depeursinge, C. Digital holographic microscopy: a noninvasive contrast imaging technique allowing quantitative visualization of living cells with sub-wavelength axial accuracy. Opt Lett 30, 468-470 (2005).
Popescu, G., Ikeda, T., Dasari, R. R. & Feld, M. S. Diffraction phase microscopy for quantifying cell structure and dynamics. Opt Lett 31, 775-777 (2006).
Rappaz, B., Marquet, P., Cuche, E., Emery, Y., Depeursinge, C. & Magistretti, P. J. Measurement of the integral refractive index and dynamic cell morphometry of living cells with digital holographic microscopy. Optics Express 13, 9361-9373 (2005).
Cuche, E., Marquet, P. & Depeursinge, C. Simultaneous amplitude-contrast and quantitative phase-contrast microscopy by numerical reconstruction of Fresnel off-axis holograms. Appl Opt 38, 6994-7001 (1999).
Colomb, T., Monfort, F., Kuhn, J., Aspert, N., Cuche, E., marian, A., Charriere, F., Bourquin, S., Marquet, P. & Depeursinge, C. Numerical parametric lens for shifting, magnification, and complete aberration compensation in digital holographic microscopy. Journal of the Optical Society of America a-Optics Image Science and Vision 23, 3177-3190 (2006).

Barer, R. Determination of dry mass, thickness, solid and water concentration in living cells. Nature 172, 1097-1098 (1953).

Popescu, G., Park, Y., Lue, N., Best-Popescu, C., Deflores, L., Dasari, R. R., Feld, M. S. & Badizadegan, K. Optical imaging of cell mass and growth dynamics. American journal of physiology 295, C538-544 (2008).

Sigel, E., Baur, R., Trube, G., Mohler, H. & Malherbe, P. The effect of subunit composition of rat brain GABAA receptors on channel function. Neuron 5, 703-711 (1990).

Malherbe, P., Sigel, E., Baur, R., Persohn, E., Richards, J. G. & Mohler, H. Functional characteristics and sites of gene expression of the alpha 1, beta 1, gamma 2-isoform of the rat GABAA receptor. J Neurosci 10, 2330-2337 (1990).

Rappaz, B., Barbul, A., Emery, Y., Korenstein, R., Depeursinge, C., Magistretti, P. J. & Marquet, P. Comparative study of human erythrocytes by digital holographic microscopy, confocal microscopy, and impedance volume analyzer. Cytom Part A 73A, 895-903 (2008).

Davies, H. G. & Wilkins, M. H. Interference microscopy and mass determination. Nature 169, 541 (1952).

Krishek, B. J., Amato, A., Connolly, C. N., Moss, S. J. & Smart, T. G. Proton sensitivity of the GABA(A) receptor is associated with the receptor subunit composition. The Journal of physiology 492 (Pt 2), 431-443 (1996).

Huang, R. Q. & Dillon, G. H. Effect of extracellular pH on GABA-activated current in rat recombinant receptors and thin hypothalamic slices. Journal of neurophysiology 82, 1233-1243 (1999).

Helix, N., Strobaek, D., Dahl, B. H. & Christophersen, P. Inhibition of the endogenous volume-regulated anion channel (VRAC) in HEK293 cells by acidic diaryl-ureas. The Journal of membrane biology 196, 83-94 (2003).

Gillen, C. M. & Forbush, B., 3rd. Functional interaction of the K-Cl cotransporter (KCC1) with the Na-K-Cl cotransporter in HEK-293 cells. The American journal of physiology 276, C328-336 (1999).

Heo, J., Meng, F. & Hua, S. Z. Contribution of aquaporins to cellular water transport observed by a microfluidic cell volume sensor. Analytical chemistry 80, 6974-6980 (2008).

The invention claimed is:

1. Apparatus for monitoring fluxes of ionic current comprising:
    a source of electromagnetic radiation,
    a passage adapted to let ionic current flow therein, and
    electromagnetic radiation phase or refractive index measuring means, all previously cited elements being arranged in a way that an electromagnetic radiation emitted by said source successively crosses said passage and enters said electromagnetic radiation phase or refractive index measuring means, and
    wherein the apparatus further includes a calculator to apply a mathematical model to determine an ionic current flux, said mathematical model determining the ionic current flux based on the first temporal derivative of a measured signal, said measured signal providing the temporal evolution of one of: the refractive index, the phase or the optical path length.

2. Apparatus according to claim 1 wherein said electromagnetic radiation phase or refractive index measuring means is adapted to detect a phase shift on an electromagnetic radiation.

3. Apparatus according to claim 2 wherein said electromagnetic radiation phase or refractive index measuring means is a wavefront sensor or an instrument based on lateral shearing interferometry, or a common-path interferometer, or a device converting stacks of intensity images in a quantitative phase image, or a Fourier Phase Microscope, or a Diffraction Phase Microscope.

4. Apparatus according to claim 2 wherein said electromagnetic radiation phase or refractive index measuring means is adapted to generate an interference between at least two electromagnetic radiations, namely:
    at least one probing beam which is arranged in a way as to interact with the ionic current,
    at least one reference beam which is arranged in a way as to not interact with the ionic current.

5. Apparatus according to claim 4 wherein said electromagnetic radiation phase or refractive index measuring means is a digital holographic microscope, or an interference microscope, or a holomonitor, or a heterodyne Mach-Zehnder phase microscope, or a Hilbert phase microscope.

6. Apparatus according to claim 1 comprising at least two different electromagnetic radiations of different wavelengths and which are adapted to be emitted simultaneously by at least two sources, or to be emitted sequentially by use of at least one tunable source.

7. Method for monitoring fluxes of ionic current, comprising the apparatus of claim 1, said method comprising the emission of at least one electromagnetic radiation through a flux of ionic current and measuring said electromagnetic radiation in order to detect phase or refractive index changes.

8. Method according to claim 7 wherein said flux is crossing at least one semipermeable membrane separating at least two media, the signals extracted from said two media being then compared to monitor or to measure fluxes of ionic current.

9. Method according to claim 7 comprising a step consisting in comparing signals extracted from at least two different regions, and wherein at least one region is a region without flux of ionic current.

10. Method according to claim 7 wherein the measured signal is considered only over a limited period of time, said measured signal providing the temporal evolution of one of: the refractive index, the phase or the optical path length.

11. A method of monitoring fluxes of ionic current, comprising the apparatus of claim 1, said method comprising: adapting said passage for monitoring fluxes of ionic current crossing the membrane of a biological cell.

12. A method of monitoring fluxes of ionic current, comprising the apparatus of claim 1, said method comprising: adapting said passage for monitoring transmembrane ionic currents associated to the electrical activity of one or several biological cells.

13. Method according to claim 11 further comprising a decoupling procedure that enables to evaluate separately cellular refractive index changes and cellular volume changes.

14. Method according to claim 7, including the step of the determining whether the ionic current flux is an inward or outward directional current flux in the passage.

15. Method according to claim 14, wherein whether an incremental or decremental change occurs in the electromagnetic radiation phase, refractive index or optical path length is determined to establish whether the ionic current flux is an inward or outward current flux in the passage.

16. Apparatus according to claim 1, wherein the calculator further determines whether the ionic current flux is an inward or outward directional current flux in the passage.

17. Apparatus according to claim 16, wherein the calculator determines whether an incremental or decremental change occurs in the electromagnetic radiation phase, refractive index or optical path length to determine whether the ionic current flux is an inward or outward current flux in the passage.

18. Method according to claim 7, comprising detecting phase changes on said electromagnetic radiation which has crossed said flux.

* * * * *